United States Patent [19]

Vale, Jr. et al.

[11] Patent Number: 5,132,111
[45] Date of Patent: Jul. 21, 1992

[54] CRF ANALOG CONJUGATES

[75] Inventors: Wylie W. Vale, Jr.; Jean E. F. Rivier, both of La Jolla, Calif.; Jeffrey Schwartz, Freehold, N.J.

[73] Assignee: The Salk Institute for Biological Studies, San Diego, Calif.

[21] Appl. No.: 508,258

[22] Filed: Apr. 11, 1990

Related U.S. Application Data

[63] Continuation-in-part of Ser. No. 65,273, Jun. 22, 1987, abandoned.

[51] Int. Cl.$^5$ .................. C12P 21/00; C07K 7/38
[52] U.S. Cl. .................. 424/85.91; 530/306; 530/324; 530/350; 530/402; 530/807; 514/805; 930/70; 930/280; 930/DIG. 570
[58] Field of Search .............. 530/306, 324, 807, 350, 530/402; 514/805; 424/85.91; 930/70, DIG. 570, 280

[56] References Cited

U.S. PATENT DOCUMENTS

| | | | |
|---|---|---|---|
| 4,468,382 | 8/1984 | Bacha et al. | 514/19 |
| 4,507,234 | 3/1985 | Kato et al. | 530/363 |
| 4,543,211 | 9/1985 | Kato et al. | 530/390 |
| 4,582,703 | 4/1986 | Jansen et al. | 424/85.91 |
| 4,594,329 | 10/1986 | Vale, Jr. et al. | 514/12 |
| 4,605,642 | 8/1986 | Rivier et al. | 514/12 |
| 4,664,911 | 5/1987 | Uhr et al. | 424/85.91 |
| 4,675,400 | 6/1987 | Cullinan | 540/478 |

OTHER PUBLICATIONS

Stirpe, et al., "Gelonin, a New Inhibitor of Protein Synthesis, Nontoxic to Intact Cells", J. Biol. Chem. 255, pp. 6947-6953 (1980).

Schwartz, et al., "Identification of Corticotropin-Releasing Factor (CRF) Target Cells and Effects of Dexamethasone on Binding in Anterior Pituitary Using A Fluorescent Analog of CRF, Endocrinology", 119, pp. 2376-2382 (1986).

Oeltmann, "Synthesis and In Vitro Activity of a Hormone-Diphtheria Toxin Fragment A Hybrid", Biochem. Biophys. Res. Comm., 133, 430-435 (1985).

Killen, et al., "Specific Killing of Lymphocytes That Cause Experimental Autoimmune Myasthenia Gravis by Ricin Toxin-Acetylcholine Receptor Conjugates," J. Immunol., 133, 2549-2553 (1984).

Colombatti, et al., "Selective Killing of Target Cells by Antibody-Ricin A Chain or Antibody Gelonin Hybrid Molecules: Comparison of Cytotoxic Potency and Use in Immunoselection Procedures", J. Immunol., 131, 3091-3095 (1983).

Uchida, et al., "Formation of a Hybrid Toxin from Ricin Agglutinin and a Non-Toxic Mutant Protein of Diphtheria Toxin", Chem. Abstracts, 89, 1445y (1978).

Schwartz, et al. "A New Cytotoxin Specific for the Target Cells of Corticotropin-Releasing Factor", Endocrinology, 121, 1454-1460 (1987).

Primary Examiner—Lester L. Lee
Assistant Examiner—T. D. Wessendorf
Attorney, Agent, or Firm—Fitch, Even, Tabin & Flannery

[57] ABSTRACT

Agonists and antagonists of rCRF are disclosed that exhibit good binding affinity to CRF receptors. One exemplary agonist is: H-Ser-Gln-Glu-Pro-Pro-Ile-Ser-Leu-Asp-Leu-Thr-Phe-His-Leu-Leu-Arg-Glu-Met-Leu-Glu-Met- Ala-Arg-Ala-Glu-Gln-Glu-Ala-Glu-Gln-Ala-Ala-Leu-Asn-Arg- Leu-Leu-Leu-Glu-Glu-Ala-NH$_2$. In the agonists, one or more of the first five N-terminal residues may be deleted or may be substituted by a peptide up to 10 amino acids long. A number of other substitutions may also be made throughout the chain. Similar peptides which function as CRF antagonists are created by deleting the first 7, 8 or 9 N-terminal residues. These analogs are coupled to a cytotoxin, such as gelonin, by a dialdehyde or the like, e.g., glutaraldehyde. The conjugates may be used to eliminate CRF Target Cells, and thus to regulate secretion of ACTH, β-lipotropin and the like. Such conjugates can also be administered to alleviate conditions associated with hyperactivity of the hypothalamus-pituitary adrenal axis as well as neoplastic diseases associated with tumors that express CRF receptor.

5 Claims, No Drawings

CRF ANALOG CONJUGATES

This invention was made with Government support under Grants Nos. AM-27641 and HL-06808 awarded by the National Institutes of Health. The Government has certain rights in this invention.

This application is a continuation-in-part of application Ser. No. 07/065,273, filed Jun. 22, 1987, now abandoned.

The present invention relates generally to peptides having high binding affinity for receptors for human corticotropin-releasing factor (CRF). In particular, the present invention is directed to CRF peptides devoid of side-chain amino groups which have high binding affinity for CRF receptors. The present invention is further directed to CRF cytotoxic conjugates, the CRF peptide(s) of which conjugates are covalently linked, exclusively through the N-terminus alpha amino group of the peptide, to a cytotoxin, which conjugates can efficiently deliver the cytotoxin to a cell with CRF receptors.

BACKGROUND OF THE INVENTION

The hypothalamus plays a key role in the regulation of adenohypophysial corticotropic cells secretory functions Factors in hypothalamus increase the rate of ACTH secretion by the pituitary gland A physiologic corticotropin releasing factor (CRF), i.e., ovine CRF (oCRF), was characterized in 1981 and disclosed in U.S. Pat. No. 4,415,558 to have the formula: H-Ser-Gln-Glu-Pro-Pro-Ile-Ser-Leu-Asp-Leu-Thr-Phe-His -Leu-Leu-Arg-Glu-Val-Leu-Glu-Met-Thr-Lys-Ala-Asp-Gln -Leu-Ala-Gln-Gln-Ala-His-Ser-Asn-Arg-Lys-Leu-Leu-Asp-Ile-Ala-NH$_2$.

Rat CRF(rCRF) has been characterized as having the formula: H-Ser-Glu-Glu-Pro-Pro-Ile-Ser-Leu-Asp-Leu-Thr -Phe-His-Leu-Leu-Arg-Glu-Val-Leu-Glu-Met-Ala-Arg-Ala-Glu -Gln-Leu-Ala-Gln-Gln-Ala-His-Ser-Asn-Arg-Lys-Leu-Met-Glu-Ile-Ile-NH$_2$ and may alternatively be referred to as rat Amunine. The formula of human CRF has been determined to be the same as that of rCRF. Synthetic rCRF and oCRF stimulate ACTH and $\beta$-endorphin activities in vitro and in vivo and substantially lower blood pressure for an extended time period Both of these hypophysiotropic factors have been reproduced by total synthesis, and analogs of the native structures have been synthesized and tested. Since these discoveries, CRF peptide analogs have been synthesized which have a high binding affinity for CRF-receptors and which are more potent and longer acting than the native hormones; research in this area is continuing.

Physiologists have known the cytotoxic effects of ricin and gelonin since 1974 and 1980, respectively. Both ricin A chain, the chain that carries the cytotoxic activity, and gelonin are inhibitors of protein synthesis and have similar molecular weights and functional properties. Ricin A chain is the more potent of the two. Both cytotoxins previously have been conjugated to antibodies and are described in the literature. Gelonin is described in *J. Biol. Chem.*, 255, 14, 6947–6953 (1980).

Cytotoxins are generally only toxic to a cell when present in the cytoplasm. It is known to deliver cytotoxins to the cytoplasm by contacting an intact cell with a cytotoxic conjugate comprising a cytotoxin and a bioactive molecule (e.g. immunoglobulin or hormone). Such cytotoxic conjugates have an affinity for a target cell which expresses on its surface a molecule which forms a binding pair with the bioactive molecule of the conjugate (e.g., an antigen or hormone receptor) and the conjugate is transported to the cytoplasm, presumably by endocytosis See Uhr et al., U.S. Pat. No. 4,664,911 and Bacha et al., U.S. Pat. No. 4,468,382.

Importantly, the bioactive component of the cytotoxic conjugate must be linked to the cytotoxin without adversely affecting binding affinity of the former. This problem is of more concern with respect to hormones, which characteristically are small peptides having a molecular weight of less than 5,000–10,000 daltons, whereas immunoglobulins are relative large proteins having molecular weights typically greater than 100,000 daltons. Consequently, the probability of successfully conjugating a bioactive molecule to a cytotoxin without adversely affecting the binding capacity of the bioactive molecule is greater in the case of immunoglobulin-cytotoxic conjugates than in the case of hormone-cytotoxic conjugates. In other words, as compared to a peptide hormone, the larger immunoglobulin protein will, on the average, have more amino acid residues available for linkage at positions which will not adversely affect its bioactivity (i.e., its capacity for binding antigen with high affinity). Thus, with respect to making hormone-cytotoxin conjugates having high binding affinity for the native receptor, if conjugation occurs through an amino-acid residue near the portion of the hormone which is critical for high affinity binding, the resultant conjugate will lack substantial capacity for binding native hormone receptor.

Furthermore, where more than one amino acid residue of the hormone is capable of forming a covalent linkage with a linker employed to form a hormone-cytotoxin conjugate, undesirable cross-linked polymers of the hormone may be formed, which may substantially preclude the capacity to bind the native hormone receptor.

Heterobifunctional linkers have been used to cause a linker to bind to particular amino acid residues (e.g., histidines) of one member of the conjugate. Bacha et al., supra, disclose a disulfide-linked, thyrotropin releasing hormone-cytotoxin conjugate which is prepared by: (i) disulfide-derivatizing the hormone (through available histidine residues) using a heterobifunctional coupling agent, (ii) disulfide-derivatizing a cytotoxin using a different heterobifunctional coupling agent, and (iii) carrying out a disulfide replacement reaction between the derivatized hormone (provided as a sulfhydryl derivative) and the derivatized cytotoxin (provided as a disulfide derivative) to form the hormone-cytotoxin conjugate.

But, despite the use of such heterobifunctional linkers it can not be predicted that the resultant hormone-cytotoxin conjugates will retain high-affinity binding capacity for the hormone's native receptor, since conjugation is directed to e.g., all available histidine residues in the peptide hormone. Therefore, if a portion of the hormone necessary for high-affinity binding of receptor comprises one or more histidine residues, the resulting conjugate will lack such binding capacity due to the addition bulk or steric hindrance presented by a massive cytotoxin molecule.

Moreover, where the hormone has more than one amino acid residue capable of reacting with a coupling agent employed in the conjugation, and thus is caused to be coupled at more than one position, upon conjugation of the "derivatized" hormone to a cytotoxin, the hormone may be linked in a sterically hindered conformation due to conjugation at the more than one "derivatized" residues of the hormone, or may be linked to more than one cytotoxin molecule, again, undesirably placing conformational constraints on the hormone which may adversely affect binding. Likewise, if a hormone has more than one reactive residue, it is probable that undesirable polymers of hormone-toxin conjugate will result (e.g., hormone-toxin-hormone$_n$), which polymers analogously lack high affinity binding capacity.

SUMMARY OF THE INVENTION

The inventors have discovered CRF-cytotoxic conjugates which have very high affinity for CRF receptors, and which conjugates do not exhibit these undesirable polymerization and/or cross-linking anomalies. The CRF-cytotoxic conjugates of the present invention comprise at least one, and preferably a plurality of CRF analog peptides, which are covalently bonded to a cytotoxic protein in a manner that does not detract from the high binding affinity which the C-terminal portion the peptide hormone exhibits for native CRF receptor.

The C-terminus of CRF is critical for binding CRF receptor with high affinity. Native CRF contains two histidine residues, one of which is near the C-terminus portion of CRF, and at least one lysine residue near the C-terminus. Thus, although histidine and lysine residues may potentially serve as amino acids through which a hormone-cytotoxin might be conjugated, for the reasons discussed above relating to maintenance of receptor binding capacity and preclusion of polymer formation, a CRF-cytotoxin conjugate having high binding affinity for CRF receptor cannot be made by linking the conjugate through histidine or lysine residues. At best, such a conjugate would possess undesirably low affinity for native CRF receptors due to undesirable conformational constraints introduced by the presence of a bulky cytotoxin component near the C-terminus of a CRF peptide. In the CRF-cytotoxic conjugates of the present invention, the CRF analog molecules are coupled substantially exclusively through the alpha amino group of the 1-position amino acid (i.e., the N-terminus) thus allowing the critical C-terminus of the CRF analog molecule to adopt a conformation necessary to provide the high affinity receptor binding capacity.

The inventors have achieved all of the above benefits by providing CRF analog peptides that are devoid of side-chain primary amino groups, yet retain high affinity for CRF receptors. This, in turn, allows conjugation to be directed exclusively to the sole primary amino group of the CRF analog peptides of the invention, thus ensuring that the conjugates of the invention are coupled substantially only through the 1-position. Moreover, the CRF-cytotoxin conjugates of the invention may be made with inexpensive linking agents (e.g, glutaraldehyde), instead of costly heterobifunctional linkers.

Certain synthetic polypeptides have now been synthesized and tested which exhibit a high binding affinity for CRF receptors on CRF Target Cells in a culture of pituitary cells and which may be effectively chemically linked to a toxin. By high binding affinity is meant a $K_a = 1 \times 10^7 M^{-1}$ or less, i.e. at least 50% of all specific binding sites are occupied at concentrations of the peptides of about $10^{-7}$ molar. These peptides may contain from 32 to 41 amino acid residues and are devoid of side-chain primary amino groups, such that they utilize only the alpha amino group at the N-terminus to effect conjugation to a separate protein.

Conjugation of a cytotoxin such as ricin A chain or gelonin to a CRF analog is realized through synthesis of a CRF analog devoid of side-chain primary amino groups, which CRF analog will link to the cytotoxic protein only via its N-terminus amino group. Linking of the free alpha-amino group of the N-terminal amino acid to the protein by a dialdehyde, e.g., glutaraldehyde, is preferred, but other difunctional conjugating compounds, e.g., diacids, can be used.

The conjugate retains the high binding affinity for CRF receptors, and carries the characteristic inhibitory effect on protein synthesis within a cell of the cytotoxin. The cytotoxic effect is believed to be ultimately realized when a cell ingests the bound conjugate through the process of endocytosis. More specifically, CRF peptide analogs with positions 23 and 36 devoid of amino functions, for example, [Nle21,38, Arg$^{36}$]-rCRF or [Nle$^{21}$, Arg$^{23,36}$]-oCRF can be coupled to a cytotoxic protein through the N-terminal alpha amino group using glutaraldehyde. The cytotoxic protein employed is chosen for its ability to kill cells by interfering with DNA replication by inhibiting protein synthesis by likely binding to the ribosome.

The CRF peptide analogs used in the invention may also have substitutions for a number of other residues which appear in natural CRF sequences as generally set forth in U.S. Pat. No. 4,594,329, the disclosure of which is incorporated herein by reference. Moreover certain of the Ala and/or Leu residues may have a methyl substitution on their alpha-carbon atoms.

Pharmaceutical compositions in accordance with the invention include such analogs which are at least 32 residues in length devoid of any side-chain amino functions and coupled, as by glutaraldehyde-coupling, to a cytotoxic protein through the alpha amino group at the N-terminus, dispersed in a pharmaceutically or veterinarily acceptable liquid or solid carrier. Such pharmaceutical compositions can be used in clinical medicine, both human and veterinary, for administration for therapeutic purposes, as for example, to treat or to modulate CRF Target Cells, which possess CRF receptors, 20 which constitute about 6% of the total anterior pituitary cells, see J. Schwartz et al. *Endocrinology*, 119, 5, pp 2376-2382 (1986). Such conjugates may be used to regulate secretion of ACTH, $\beta$-endorphin, $\beta$-lipotropin, other products of the pro-opiomelanocortin gene and corticosterone and/or for the lowering of blood pressure and/or for affecting mood, behavioral and gastro-intestinal functions and autonomic nervous system activities.

DETAILED DESCRIPTION OF PREFERRED EMBODIMENTS

The nomenclature used to define the peptides is that specified by Schroder & Lubke, "The Peptides", Academic Press (1965) wherein, in accordance with conventional representation, the amino group appears to the left and the carboxyl group to the right. The standard 3-letter abbreviations to identify the alpha-amino acid residues, and where the amino acid residue has isomeric forms, it is the L-form of the amino acid that is represented unless otherwise expressly indicated, e.g. Ser = L-serine, Nle = L-norleucine, Nva = norvaline, Har = homoarginine, Orn = ornithine etc. In addition the following abbreviations are used: leu = either L-leucine or C$^a$CH$_3$-L-leucine (CML) and ala = either L-alanine or C$^a$CH$_3$-L-alanine(CMA).

Analogs of the 41-residue CRF peptides having the following formula exhibit a high binding affinity for CRF receptors and, depending upon the composition of Q, either have at least substantially the same biological activity in the foregoing respects as the native peptides or are competitive antagonists of the natural peptides:

Q-leu-$R_{11}$-$R_{12}$-$R_{13}$-leu-leu-Arg-Glu-$R_{18}$-$R_{19}$ -Glu-$R_{21}$-$R_{22}$-$R_{23}$-$R_{24}$-$R_{25}$-$R_{26}$-$R_{27}$-$R_{28}$-$R_{29}$-Gln-ala-$R_{32}$-$R_{33}$-Asn-Arg-$R_{36}$-$R_{37}$-$R_{38}$-$R_{39}$-$R_{40}$-$R_{41}$-$NH_2$ wherein Q is $R_1$-$R_2$-$R_3$-$R_4$-$R_5$-Ile-Ser-$R_8$-$R_9$ or Ser-$R_8$-$R_9$ or $R_8$-$R_9$ or $R_8$ or $R_9$ or desQ; $R_1$ is Ser, D-Ser or desR$_1$; $R_2$ is Gln, pGlu, Glu, D-pGlu or desR$_2$; $R_3$ is Glu, Gly, D-Tyr or desR$_3$; $R_4$ is Pro, D-Pro or desR$_4$; $R_5$ is Pro or desR$_5$; $R_8$, $R_{12}$, $R_{19}$ and $R_{24}$ are selected from the group consisting of leu, Ile, ala, Gly, Val, Nle, Phe and Gln; $R_9$ is Asp or Glu; $R_{11}$ is Thr or Ser; $R_{13}$ is His, Tyr or Glu; $R_{18}$ is Val, Nle or Met; $R_{21}$ is Met, Nva, Ile, ala, leu, Nle, Val, Phe or Gln; $R_{22}$ is ala, Thr, Asp or Glu; $R_{23}$ is Arg or Har; $R_{25}$ is Asp or Glu; $R_{26}$ is Gln or Asn; $R_{27}$ is leu, Ile, ala, Val, Nva, Met, Nle, Phe, Asp, Asn, Gln or Glu; $R_{28}$ is ala or Arg; $R_{29}$ is Gln or Glu, $R_{32}$ is His, Gly, Tyr or ala; $R_{33}$ is Ser, Asn, leu, Thr or ala; $R_{36}$ is Arg, Har or Leu; $R_{37}$ is leu or Tyr; $R_{38}$ is Met, Nle or leu; $R_{39}$ is Glu or Asp; $R_{40}$ is Ile, Thr, Glu, ala, Val, leu, Nle, Phe, Nva, Gly or Gln; $R_{41}$ is ala, Ile, Gly, Val, Leu, Nle, Phe, Gln or des $R_{41}$.

CRF analog peptides of the above formula are peptides devoid of side-chain primary amino groups, which exhibit high binding affinity for CRF receptors. By "a CRF analog devoid of side-chain primary amino groups" is meant a CRF analog devoid of lysine, hydroxylysine, ornithine and any synthetic amino acid having a side-chain of the formula -R-NH$_2$ wherein R is typically an alkylene group, which primary amino group-containing side-chains are capable of forming a covalent bond with a carbonyl-containing functional group of a coupling agent. A CRF analog devoid of side-chain primary amino groups has a single free primary amino group, the N-terminal alpha amino group, which will form a covalent bond with a carbonyl-containing functional group of a difunctional coupling agent e.g., an aldehyde group of a dialdehyde. The guanidino-containing side-chain of arginine

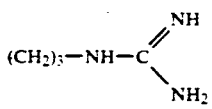

is not, and does not chemically behave like, a primary amino group. The guanidino group of arginine is substantially unreactive with, for example, aldehydes because the guanidino group is extremely basic and will not form a Schiff base with the carbonyl group of a coupling agent. Likewise, histidine does not contain a primary amino group, and peptides containing His do not react with dialdehydes.

CRF peptides devoid of side-chain primary amino groups possess precisely one free primary amino group, the N-terminal alpha-amino group, and conjugation of such CRF peptides to a cytotoxic protein provides a CRF-cytotoxic conjugate of the invention having one or more CRF peptide analogs of the invention, linked exclusively via their N-terminal primary amino groups to a cytotoxic protein.

Preferred CRF analog peptides devoid of side-chain amino groups such that the analogs may be conjugated to a cytotoxin exclusively through their N-terminal alpha amino group are [Nle$^{21,38}$, Arg$^{36}$]-rCRF, and [Nle$^{21}$, Arg$^{23,36}$]-oCRF, which have the following formulae, respectively: H-Ser-Glu-Glu-Pro-Pro-Ile-Ser-Leu-Asp-Leu-Thr -Phe-His-Leu-Leu-Arg-Glu-Val-Leu-Glu-Nle-Ala-Arg-Ala-Glu -Gln-Leu-Ala-Gln-Gln-Ala-His-Ser-Asn-Arg-Arg-Leu-Nle-Glu -Ile-Ile-NH$_2$;

and H-Ser-Gln-Glu-Pro-Pro-Ile-Ser-Leu-Asp-Leu-Thr-Phe-His -Leu-Leu-Arg-Glu-Val-Leu-Glu-Nle-Thr-Arg-Ala-Asp-Gln -Leu-Ala-Gln-Gln-Ala-His-Ser-Asn-Arg-Arg-Leu-Leu-Asp -Ile-Ala-NH$_2$.

Other CRF agonists devoid of side-chain amino groups which have been synthesized and are at least as potent as native CRF include CRF peptide analogs of the invention having the following substitutions, which peptides have a high alpha-helical forming potential: $R_1$ is Ser, $R_2$ is Gln or Glu, $R_3$ is Glu, $R_4$ and $R_5$ are Pro, $R_8$ is leu, $R_{11}$ is Thr, $R_{12}$ is Phe or leu, $R_{13}$ is His or Glu, $R_{18}$ and $R_{21}$ are Met or Nle, $R_{19}$ and $R_{37}$ are leu, $R_{22}$ and $R_{41}$ are ala, $R_{23}$ is Arg, $R_{24}$ and $R_{28}$ are ala, $R_{25}$ and $R_{39}$ are Glu, $R_{26}$ is Gln, $R_{27}$ is Glu or leu, $R_{29}$ is Glu, $R_{32}$ is His or ala, $R_{33}$ is Ser or leu, $R_{38}$ is Leu and $R_{40}$ is Ile or Glu. One analog which is particularly potent is: H-Ser-Gln-Glu-Pro-Pro-Ile-Ser-Leu-Asp-Leu-Thr-Phe-His -Leu-Leu-Arg-Glu-Met-Leu-Glu-Met-Ala-Arg-Ala-Glu-Gln-Glu -Ala-Glu-Gln-Ala-Ala-Leu-Asn-Arg-Leu-Leu-Leu-Glu-Glu-Ala-NH$_2$ and is hereinafter referred to as AAHC (for Arg$^{23}$-alpha-helical CRF); it remains potent even if shortened at the N-terminus by from one to five residues. However, if shortened to eliminate residues 1 to 7, 1 to 8 or 1 to 9, competitive antagonists of CRF are formed.

Thus, in one of its aspects the present invention includes potent CRF analogs which are devoid of side-chain primary amino groups.

In another of its aspects the invention entails CRF cytotoxic conjugates having high affinity binding capacity for an intact cell having a CRF receptor on its surface, which CRF cytotoxic conjugates comprise (i) at least one CRF analog peptide devoid of side-chain primary amino groups, said at least one CRF analog having a N-terminus free alpha-amino group and consisting of between 32 and 41 amino acid residues (ii) at least one difunctional coupling agent having a first carbonyl-containing functional group for coupling a first primary amino group, and a second carbonyl-containing functional group for coupling a second primary amino group, said first and second functional groups being independently capable of coupling said first and second primary amino groups; and (iii) a cytotoxic protein having at least one free primary amino group, wherein substantially every CRF peptide of said conjugate is covalently linked through the N-terminus alpha-amino group of the CRF peptide to the first functional group of said at least one difunctional coupling agent and wherein the second functional group of the last said coupling agent is covalently linked to said at least one primary amino group of said cytotoxic protein.

The CRF analog peptides of the invention are synthesized by a suitable method, such as by exclusively solid-phase techniques, by partial solid-phase techniques, by fragment condensation or by classical solution addition. Certain CRF analogs which do not include D-isomer residues or unnatural amino acid residues may also be synthesized by recently developed recombinant DNA techniques.

Synthesis by the use of recombinant DNA techniques, for purposes of this application, should be understood to include the suitable employment of a structural gene coding for the desired form of CRF analog. The synthetic CRF peptide may be obtained by transforming a microorganism using an expression vector including a promoter and operator together with such structural gene and causing such transformed microorganism to express the CRF peptide. A non-human animal may also be used to produce the CRF peptide by gene-farming using such a structural gene and the general techniques set forth in U.S. Pat. No. 4,276,282 issued Jun. 30, 1981 or using microinjection of embryos as described in W083/01783 published 26 May 1983 and W082/04443 published 23 December 1982. The synthetic CRF peptide is then suitably recovered from the animal by extraction from sera or the like.

Techniques of exclusively solid-phase synthesis are set forth in the textbook "Solid-Phase Peptide Synthesis", Stewart & Young, Freeman & Co., San Francisco, 1969, and are exemplified by the disclosure of U.S. Pat. No. 4,105,603, issued Aug. 8, 1978 to Vale et al. Classical solution synthesis is described in detail in the treatise "Methoden der Organischen Chemie (Houben-Weyl): Synthese von Peptiden", E. Wunsch (editor) (1974) Georg Thieme Verlag, Stuttgart, W. Ger. The fragment condensation method of synthesis is exemplified in U.S. Pat. No. 3,972,859 (Aug. 3, 1976). Other available syntheses are exemplified by U.S. Pat. No. 3,842,067 (Oct. 15, 1974) and U.S. Pat. No. 3,862,925 (Jan. 28, 1975).

Common to chemical syntheses of peptides is the protection of the labile side chain groups of the various amino acid moieties with suitable protecting groups which will prevent a chemical reaction from occurring at that site until the group is ultimately removed. Usually also common is the protection of an alpha-amino group on an amino acid or a fragment while that entity reacts at the carboxyl group, followed by the selective removal of the alpha-amino protecting group to allow subsequent reaction to take place at that location. Accordingly, it is common that, as a step in the synthesis, an intermediate compound is produced which includes each of the amino acid residues located in its desired sequence in the peptide chain with various of these residues having side-chain protecting groups.

Such chemical syntheses can produce intermediates of the Formula (II): $X^1-R_1(X^2)-R_2(X^4$ or $X^5)-R_3(X^5$ or $X^6)-R_4-R_5$-Ile-Ser($X^2$)$-R_8-R_9(X^5)$-leu-$R_{11}(X^2)$-$R_{12}(X^4)$-$R_{13}(X$ or $X^5)$-leu-leu-Arg($X^3$)-Glu($X^5$)-$R_{18}-R_{19}(X^4)$-Glu($X^5$)-$R_{2\text{-}1}-R_{22}(X^2$ or $X^5)-R_{23}(X^3)$ $-R_{24}(X^4)-R_{25}(X^5)-R_{26}(X^4)-R_{27}(X^4$ or $X^5)-R_{28}(X^3)-R_{29}(X^4$ or $X^5)$-Gln($X^4$)-Ala-$R_{32}(X^6)-R_{33}(X^2$ or $X^4)$-Asn($X^4$)-Arg($X^3$)-$R_{36}(X^3)-R_{37}(X)-R_{38}-R_{39}(X^5)-R_{40}(X^2$ or $X^4$ or $X^5)-R_{41}(X^4)-X^7$, or versions thereof which are shortened at the N-terminus as set forth hereinbefore, wherein: the R-groups are as hereinbefore defined.

$X^1$ is either hydrogen or an a-amino protecting group. The a-amino protecting groups contemplated by $X^1$ are those known to be useful in the art in the stepwise synthesis of polypeptides. Among the classes of a-amino protecting groups covered by $X^1$ are (1) acyl-type protecting groups, such as formyl, acrylyl(Acr), benzoyl(Bz) and acetyl(Ac) which are preferably used only at the N-terminal; (2) aromatic urethan-type protecting groups, such as benzyloxycarbonyl(Z) and substituted Z, such as p-chlorobenzyloxycarbonyl, p-nitrobenzyloxycarbonyl, p-bromobenzyloxycarbonyl, p-methoxybenzyloxycarbonyl; (3) aliphatic urethan protecting groups, such as t-butyloxycarbonyl (BOC), diisopropylmethoxycarbonyl, isopropyloxycarbonyl, ethoxycarbonyl, allyloxycarbonyl; (4) cycloalkyl urethan-type protecting groups, such as fluoroenylmethyloxycarbonyl(FMOC), cyclopentyloxycarbonyl, adamantyloxycarbonyl, and cyclohexyloxycarbonyl; and (5) thiourethan-type protecting groups, such as phenylthiocarbonyl. The preferred a-amino protecting group is BOC.

$X^2$ is a protecting group for the hydroxyl group of Thr and Ser and is preferably selected from the class consisting of acetyl(Ac), benzoyl(Bz), tert-butyl, triphenylmethyl(trityl), tetrahydropyranyl, benzyl ether(Bzl) and 2,6-dichlorobenzyl (DCB). The most preferred protecting group is Bzl. $X^2$ can be hydrogen, which means there is no protecting group on the hydroxyl group.

$X^3$ is a protecting group for the guanidino group of Arg or Har preferably selected from the class consisting of nitro, p-toluenesulfonyl(Tos), Z, adamantyloxycarbonyl and BOC, or is hydrogen. Tos is most preferred.

$X^4$ is hydrogen or a protecting group, preferably xanthyl(Xan), for the amido group of Asn or Gln.

$X^5$ is hydrogen or an ester-forming protecting group for the $\beta$- or gamma-carboxyl group of Asp or Glu, preferably selected from the class consisting of benzyl, 2,6-dichlorobenzyl, methyl, ethyl and t-butyl ester. OBzl is most preferred.

When His is present, $X^6$ is hydrogen or a protecting group for the imidazole nitrogen such as Tos or 2,4-dinitrophenyl(DNP), and when Tyr is present, $X^6$ is hydrogen or a protecting group for the hydroxyl group such as DCB. When Met is present, the sulfur may be protected, if desired, with oxygen.

The selection of a side chain amino protecting group is not critical except that it should be one which is not removed during deprotection of the a-amino groups during the synthesis. Hence, the a-amino protecting group and the side chain amino protecting group cannot be the same.

$X^7$ is $NH_2$, a protecting group such as an ester or an anchoring bond used in solid phase synthesis for linking to a solid resin support, preferably one represented by the formulae:

—NH-benzhydrylamine (BHA) resin support and
—NH-paramethylbenzhydrylamine (MBHA) resin support. Cleavage from a BHA or MBHA resin directly gives the CRF analog amide. By employing a methyl-derivative of such a resin, a methyl-substituted amide can be created.

In the formula for the intermediate, at least one of X, $X^1$, $X^2$, $X^3$, $X^4$, $X^5$ and $X^6$ is a protecting group. The particular amino acid chosen for each the R-group determines whether there will also be a protecting group attached as specified hereinbefore and as generally known in the art. In selecting a particular side chain protecting group to be used in the synthesis of the peptides, the following rules are followed: (a) the protecting group should be stable to the reagent and under the reaction conditions selected for removing the a-amino protecting group at each step of the synthesis, (b) the protecting group should retain its protecting properties and not be split off under coupling conditions and (c) the side chain protecting group must be removable, upon the completion of the synthesis containing the desired amino acid sequence, under reaction conditions that will not alter the peptide chain.

Thus, a process is provided for first manufacturing a compound defined by the Formula (I) by (a) forming a peptide having at least one protecting group and having the Formula (II) wherein: $X^1$, $X^2$, $X^3$, $X^4$, $X^5$ and $X^6$ are each either hydrogen or a protecting group, and $X^7$ is either a protecting group or an anchoring bond to resin support or $NH_2$ and (b) splitting off the protective group or groups or anchoring bond from said peptide of the Formula (II) and then (c) converting the resulting peptide into a conjugate with a cytotoxic protein via dialdehyde linkage.

When the peptides are prepared by chemical synthesis, they are preferably prepared using solid phase synthesis, such as that described by Merrifield, *J. Am. Chem. Soc.*, 85, p 2149 (1964), although other equivalent chemical syntheses known in the art can also be used as previously mentioned. Solid-phase synthesis is commenced from the C-terminal end of the peptide by coupling a protected a-amino acid to a suitable resin as generally set forth in U.S. Pat. No. 4,244,946 issued Jan. 21, 1981 to Rivier et al., the disclosure of which is incorporated herein by reference. Such a starting material for rCRF analogs can be prepared by attaching a-amino-protected Ile to a BHA resin.

Ile protected by BOC is coupled to the BHA resin using methylene chloride and dimethylformamide (DMF). Following the coupling of BOC-Ile to the resin support, the a-amino protecting group is removed, as by using trifluoroacetic acid(TFA) in methylene chloride, TFA alone or with HCl in dioxane. Preferably 50 volume % TFA in methylene chloride is used with 0–5 weight % 1,2 ethanedithiol. The deprotection is carried out at a temperature between about 0 C and room temperature. Other standard cleaving reagents and conditions for removal of specific a-amino protecting groups may be used as described in Schroder & Lubke, "The Peptides", 1 pp 72–75 (Academic Press 1965).

After removal of the a-amino protecting group of Ile, the remaining a-amino- and side chain-protected amino acids are coupled step-wise in the desired order to obtain the intermediate compound defined hereinbefore. As an alternative to adding each amino acid separately in the synthesis, some of them may be coupled to one another prior to addition to the solid phase reactor. The selection of an appropriate coupling reagent is within the skill of the art. Particularly suitable as coupling reagents are N,N'-dicyclohexyl carbodiimide(DCCI) and N,N'-diisopropyl carbodiimide(DICI).

The activating reagents used in the solid phase synthesis of the peptides are well known in the peptide art. Examples of suitable activating reagents are carbodiimides, such as N,N'-diisopropyl carbodiimide and N-ethyl-N'-(3-dimethylaminopropyl)carbodiimide. Other activating reagents and their use in peptide coupling are described by Schroder & Lubke, supra, in Chapter III and by Kapoor, *J. Phar. Sci.*, 59, pp 1–27 (1970).

Each protected amino acid or amino acid sequence is introduced into the solid phase reactor in about a four-fold excess, and the coupling is carried out in a medium of dimethylformamide(DMF):$CH_2Cl_2$ (1:1) or in DMF or $CH_2Cl_2$ alone. In instances where the coupling is carried out manually, the success of the coupling reaction at each stage of the synthesis is monitored by the ninhydrin reaction, as described by E. Kaiser et al., *Anal. Biochem.* 34, 595 (1970). In cases where incomplete coupling occurs, the coupling procedure is repeated before removal of the a-amino protecting group prior to the coupling of the next amino acid. The coupling reactions can be performed automatically, as on a Beckman 990 automatic synthesizer, using a program such as that reported in Rivier et al., *Biopolymers*, 17, 1927–1938 (1978).

After the desired amino acid sequence has been completed, the intermediate peptide is removed from the resin support by treatment with a reagent, such as liquid hydrogen fluoride, which not only cleaves the peptide from the resin but also cleaves all remaining side chain protecting groups $X^2$, $X^3$, $X^4$, $X^5$ and $X^6$ and the a-amino protecting group $X^1$ to obtain the peptide. When using hydrogen fluoride for cleaving, anisole or cresole and methylethyl sulfide are included in the reaction vessel as scavengers. When Met is present in the sequence, the BOC protecting group may be cleaved with trifluoroacetic acid(TFA)/ethanedithiol prior to cleaving the peptide from the resin to eliminate S-alkylation.

The CRF peptide analogs of the invention are conjugated to a cytotoxic protein using a difunctional coupling agent which is chemically reactive with primary amino groups. By "difunctional coupling agent" is meant a chemical linking agent which has two linking groups each of which is capable of forming a covalent bond with a primary amino group of a peptide/protein such that the coupling agent links two peptide/protein molecules. Difunctional coupling agents employed in the CRF cytotoxic conjugates of the invention include compounds having two carbonyl-containing functional groups; for example, dialdehydes and diacids. Dialdehydes are preferred. It is well known that the functional groups of such coupling agents are capable of reacting with and forming covalent bonds with primary amino groups.

A bridging group separates the two functional groups of the coupling agent such that when one functional group of the difunctional coupling agent covalently bonds to the N-terminal alpha amino group of a CRF analog of the invention, the other functional group of the difunctional coupling agent is available for covalently bonding a primary amino group of the cytotoxin (i.e., a lysine epsilon amino, the N-terminus alpha amino, etc.) . The bridging group may be an alkylene group of 1–20 carbon atoms or a cycloalkylene group of 3–20.

Especially preferred are compounds of the formulae $HOOC(CH_2)_nCOOH$ or $OHC(CH_2)_nCHO$, where n is an integer between 2 and 6. Glutaraldehyde is most preferred. Such difunctional coupling agents are well known to the person of ordinary skill in the art.

CRF-cytotoxic conjugates of the present invention may be conjugated in essentially a two-step procedure. First, CRF is "activated" to form a covalent bond between the N-terminus alpha amino of CRF and a functional coupling group of the difunctional coupling agent. Second, "activated" CRF molecules are reacted with a cytotoxic protein to form a CRF-cytotoxic conjugate of the invention.

CRF peptides devoid of side-chain primary amino groups may be conjugated, employing these difunctional coupling agents, substantially exclusively through the N-terminal alpha amino group of a CRF peptide to a primary amino group of a cytotoxic protein. Preferably a cytotoxic protein will have a plurality of primary amino groups, so that a plurality of CRF peptides may be coupled thereto.

CRF peptides are "activated" by mixing a large molar excess of the difunctional linker and a CRF peptide analog of the invention. The reaction between difunctional coupling agent and CRF is carried out for 1-10 minutes at 20°-35° C., preferably for 4-6 minutes at 25° C. in a phosphate buffered saline solution (e.g., 0.14M NaCl, 5mM sodium phosphate pH 7.4) to which a suitable organic solvent such as acetonitrile may be added, if necessary, to solubilize the peptide. The product of the reaction is predominantly "activated" CRF molecule, that is, CRF linked to one functional group of the difunctional coupling agent. Assuming glutaraldehyde and [Nle$^{21,38}$,Arg$^{36}$]-rCRF are reacted, the predominant product will be [OHC-(CH$_2$)$_5$-Ser$^1$Nle$^{21,3}$-$^8$,Arg$^{36}$]rCRF. Other expected products which may be formed in relative minor quantity in the "activation" reaction include polymers of the coupling agent (e.g., glutaraldehyde polymers) which are conveniently removed during ultrafiltration "washes" which immediately follow "activation." Also, dimers of activated CRF analog (e.g, CRFSer$^1$-(CH$_2$)$_5$-Ser$^1$CRF), may be formed. However, the dimers lack primary amino groups and therefore, which cannot further react to form conjugates. Thus, formation of undesirable polymers is precluded, and the dimers may be removed during a subsequent ultrafiltration step. After the "activation" reaction is carried out for an appropriate amount of time, the reaction mixture is precipitated with cold phosphate buffered saline (4.C.).

The activated-peptide-containing mixture is then washed, preferably twice, by ultrafiltration by (1000 MW cut-off filter Amicon ultrafiltration cell, Danvers, Mass.) with 0.14M NaCl, 5mM sodium phosphate buffer, and the mixture containing the activated CRF is concentrated to a small volume (e.g., 300 μl) again by ultrafiltration. The precipitated, activated CRF in the mixture is then redissolved by the addition of, for example, acetonitrile; and a cytotoxic protein containing at least one, preferably a plurality of, primary amino group(s) for example, ricin A-chain or gelonin, is added and the solution stirred overnight at 20°-30° C.

Gelonin is the most preferred cytotoxin CRF-gelonin conjugates of the present invention are characterized in that they may contain up to about 20 molecules of CRF per molecule of gelonin. Where ricin A-chain or other cytotoxic protein is employed, the person of ordinary skill in the art may readily determine the number of primary amino groups in the cytotoxin and calculate a suitable ratio of molar concentration of cytotoxic protein to the molar concentration of a defined CRF analog which will result in at least one, and preferably a plurality of, activated CRF molecule(s) covalently linking to one cytotoxic protein molecule; most preferably the ratio of molar concentrations of CRF analog and cytotoxic protein are adjusted so that on the average the maximum number of available lysine residues (and/or other available primary amino groups) in the cytotoxic protein are covalently bound by the activated CRF peptides of the invention. After the conjugation reaction is completed, the conjugates are washed thoroughly by ultrafiltration using a filter having a suitable MW cut-off (e.g., a 30,000 MW cut-off in the case of a CRF-gelonin conjugate). CRF dimer not removed during the prior ultrafiltration washes are removed in this step.

CRF cytotoxic conjugates of the present invention are relatively inexpensive and easy to prepare and are surprisingly effective for specifically killing CRF-responsive cells (corticotropes). It is believed that the surprising effectiveness of the cytotoxic conjugates of the invention results because conjugation is directed to occur away from the C-terminal portion of CRF analog which is critical for high affinity of the CRF receptor. CRF-cytotoxic conjugates of the present invention may comprise a plurality of CRF analogs linked to a cytotoxic protein through the N-terminus of each CRF molecule and thereby present a plurality of bioactive hormones, any one of which possesses high binding affinity for the native receptor.

The following Example sets forth a preferred method for synthesizing CRF analogs by the solid-phase technique.

EXAMPLE I

The synthesis of $[Nle^{21,38},Arg^{35}]$-rCRF having the formula: H-Ser-Glu-Glu-Pro-Pro-Ile-Ser-Leu-Asp-Leu-Thr-Phe-His-Leu-Leu-Arg-Glu-Val-Leu-Glu-Nle-Ala-Arg -Ala-Glu-Gln-Leu-Ala-Gln-Gln-Ala-His-Ser-Asn-Arg-Arg-Leu -Nle-Glu-Ile-Ile-$NH_2$ is conducted in a stepwise manner on a MBHA hydrochloride resin, such as available from Bachem, Inc., having a substitution range of about 0.1 to 0.5 mmoles/gm. resin. The synthesis is performed on an automatic Beckman 990B peptide synthesizer using a suitable program, preferably as follows:

| STEP | REAGENTS AND OPERATIONS | MIX TIMES MIN. |
|---|---|---|
| 1 | $CH_2Cl_2$ wash-80 ml. (2 times) | 3 |
| 2 | Methanol(MeOH) wash-30 ml. (2 times) | 3 |
| 3 | $CH_2Cl_2$ wash-80 ml. (3 times) | 3 |
| 4 | 50 percent TFA plus 5 percent 1,2-ethane-dithiol in $CH_2Cl_2$-70 ml. (2 times) | 12 |
| 5 | Isopropanol wash-80 ml. (2 times) | 3 |
| 6 | TEA 12.5 percent in $CH_2Cl_2$-70 ml. (2 times) | 5 |
| 7 | MeOH wash-40 ml. (2 times) | 2 |
| 8 | $CH_2Cl_2$ wash-80 ml. (3 times) | 3 |
| 9 | Boc-amino acid (10 mmoles) in 30 ml. of either DMF or $CH_2Cl_2$, depending upon the solubility of the particular protected amino acid, (1 time) plus DCCI (10 mmoles) in $CH_2Cl_2$ | 30-300 |

Coupling of BOC-Ile results in the substitution of about mmol. Ile per gram of resin. All solvents that are used are carefully degassed, preferably by sparging with an inert gas, e.g. helium or nitrogen, to insure the absence of oxygen that might undesirably oxidize the sulfur of the Met residue.

After deprotection and neutralization, the peptide chain is built step-by-step on the resin. Generally, one to two mmol. of BOC-protected amino acid in methylene chloride is used per gram of resin, plus one equivalent of 2 molar DCCI in methylene chloride, for two hours. When BOC-Arg(Tos) is being coupled, a mixture of 50% DMF and methylene chloride is used. Bzl is used as the hydroxyl side-chain protecting group for Ser and Thr. P-nitrophenyl ester(ONp) is used to activate the carboxyl end of Asn or Gln, and for example, BOC-Asn(ONp) is coupled overnight using one equivalent of HOBt in a 50% mixture of DMF and methylene chloride. The amido group of Asn or Gln is protected by Xan when DCCI coupling is used instead of the active ester method. Tos is used to protect the guanidino group of Arg and the imidazole group of His, and the side chain carboxyl group of Glu or Asp is protected by OBzl. At the end of the synthesis, the following composition is obtained BOC-Ser(Bzl)-Glu(OBzl)-Glu(OBzl)-Pro-Pro-Ile-Ser(Bzl)-Leu-Asp (OBzl)-Leu-Thr(Bzl)-Phe-His(Tos)-Leu-Leu-Arg(Tos)-Glu (OBzl)-Val-Leu-Glu(OBzl)-Nle-Ala-Arg(Tos)-Ala-Glu (OBzl)-Gln(Xan)-Leu-Ala-Gln(Xan)-Gln(Xan)-Ala-His (Tos)-Ser(Bzl)-Asn(Xan)-Arg(Tos)-Arg(Tos)-Leu-Nle-Glu(OBzl)-Ile-Ile-resin support. Xan may have been partially or totally removed by TFA treatment used to deblock the a-amino protecting group.

In order to cleave and deprotect the resulting protected peptide-resin, it is treated with 1.5 ml. anisole, 0.5 ml. of methylethylsulfide and 15 ml. hydrogen fluoride (HF) per gram of peptide-resin, first at −20° C. for 20 min. and then at 0° C. for one-half hour. After elimination of the HF under high vacuum, the resin-peptide is washed alternately with dry diethyl ether and chloroform, and the peptides are then extracted with degassed 2N aqueous acetic acid and separated from the resin by filtration.

The peptide is purified by gel permeation followed by semi-preparative HPLC as described in Rivier et al., *Peptides: Structure and Biological Function* (1979) pp. 125–128, and Rivier et al., J. Chromatography (1983). The chromatographic fractions are carefully monitored by HPLC, and only the fractions showing substantial purity are pooled.

To check whether the precise sequence is achieved, the rCRF analog is hydrolyzed in sealed evacuated tubes containing constant boiling HCl, 3 ul of thioglycol/ml. and 1 nmol of GABA or Nle (as an internal standard) for 9 hours at 140° C. Amino acid analyses of the hydrolysates using a Beckman 121 MB amino acid analyzer shows the following amino acid content: Asx(2.03), Thr(0.93), Ser(2.62), Glx(9.60), Pro(2.0), Ala(4.0), Val(0.84), Nle(2.17), Ile(2.14), Leu(7.06), the 41-residue peptide structure is obtained.

EXAMPLE II

The synthetic peptide AAHC having the formula: H-Ser-Gln-Glu-Pro-Pro-Ile-Ser-Leu-Asp-Leu-Thr-Phe-His-Leu -Leu-Arg-Glu-Met-Leu-Glu-Met-Ala-Arg-Ala-Glu-Gln-Glu-Ala -Glu-Gln-Ala-Ala-Leu-Asn-Arg-Leu-Leu-Leu-Glu-Glu-Ala-$NH_2$ is synthesized using a procedure generally as set forth in Example I.

EXAMPLE III

The synthetic peptides resulting from Examples I and II are examined for their effects on the secretion of ACTH and β-endorphin in vitro and was also in vivo. The potency of the synthetic CRF analogs to stimulate the secretion of ACTH and β-endorphin by cultured rat pituitary cells is measured using the procedure as generally set forth in *Endocrinology*, 91, 562 (1972). In vivo testing is carried out using the general procedure set forth in C. Rivier et al., *Science*, 218, 377 (1982). The peptides are biologically potent to stimulate the secretion of both ACTH and β-endorphin.

EXAMPLE IV

The conjugation of [$Nle^{21,38}$,$Arg^{36}$]-rCRF to a cytoxic protein which interferes with protein synthesis, such as ricin A chain or gelonin, is accomplished using glutaraldehyde, which couples through primary amines. The peptide is activated by reaction with an excess of glutaraldehyde. 4 mg(720 nmol) of the CRF analog is placed in 440 ul of a 0.14M sodium chloride, 5 nM sodium phosphate reaction buffer at pH 7.4.The CRF analog completely dissolves upon addition of 150 ul of acetonitrile. 20 ul of glutaraldehyde (20 ul of a 25g/100ml of aqueous solution) is added to the reaction buffer. Cold (4° C.) sodium chloride, sodium phosphate buffer is added to precipitate the peptide, and the mixture is quickly washed twice by ultrafiltration (1000 MW cutoff filter, Amicon ultrafiltration cell, Danvers, MA) with sodium chloride, sodium phosphate buffer.

The mixture, containing the reacted peptide, is concentrated to a volume of approximately 300 ul by ultrafiltration. Acetonitrile is then added until the suspension dissolves. Gelonin (2 mg, 67 nmol) is added, and the clear solution is stirred at room temperature overnight. The reaction product is washed thoroughly by ultrafiltration with a 30,000 MW-cutoff filter in place in sodium chloride, sodium phosphate buffer.

The reaction product is analyzed by amino acid analysis. Taking advantage of the absence of the amino acids methionine, tyrosine and glycine in [$Nle^{21,3-8}$,$Arg^{36}$]-rCRF and the absence of norleucine in gelonin, it is possible to calculate the relative amounts of [$Nle^{21,38}$,$Arg^{36}$]-rCRF and gelonin in the reaction product by knowing the concentrations of methionine, tyrosine and glycine relative to that of norleucine. Moreover, knowing the amino acid contents of the two reactants, it is possible to confirm the composition of the reaction product by calculating the relative amounts of all amino acids in the putative product and comparing that to the observed amounts. The reaction product is also analyzed by radioimmunoassay for CRF, using an antibody directed against the carboxy-terminal of the molecule. Lastly, because this conjugate is expected to retain bioactivity as a secretagogue of ACTH (at least prior to killing the target cells), the acute (4 hour and 1 hour) ACTH-secretory responses to the cytotoxic conjugate are assessed in cell-culture assay with rat pituitary cells as described in Vale et al., *Methods in Enzymology*, 103, 565(1983).

Anterior pituitary cells from male Sprague-Dawley rate (200–250 g), dissociated as previously described and cultured, are used to test the efficacy and specificity of the CRF analog-gelonin conjugate. Efficacy is assessed by ability to decrease cellular content of ACTH and the ACTH-secretory response to CRF. Specificity is assessed by the absence of effects on content of luteinizing hormone (LH) and the LH-secretory response to gonadotropin releasing hormone (GnRH).

Except during manipulations, the cells are maintained at 37° C. in a water-saturated 7.5% $CO_2$ atmosphere in βPJ cell culture medium, made from a βPJ vehicle to which are added 2% fetal calf serum plus insulin (5 mg/L), transferrin (5 mg/L), parathyroid hormone (0.5 ug/L) and fibroblast growth factor (1 ug/L).

At least 6 hours after dissociation, $2.7 \times 10^6$ cells in 10 ml β-PJ in each of seven petri dishes (100×20 mm, Falcon, Oxnard, Calif.) are treated with either β-PJ vehicle, oCRF (2, 10, 50 nM final concentrations) or the CRF analog-gelonin conjugate (2, 10, 50 nM final concentrations). Twelve hours later the cells are washed three times in β-PJ, incubated 1 hour at 37° C., washed twice more and plates at $3 \times 10^5$ cells per well in Linbro 24-well tissue culture plates (Flow Laboratories, McLean, Va.) in β-BJ. The cells are cultured at 37° C. for three days, by which time the cells are firmly attached to the plates. Acute (4 hour) ACTH- and LH-secretory responses are assessed as previously described, and ACTH and LH content of cells is measured following solubilization with NP-40. Cells selected for content studies include those from all five pretreatment groups that are not exposed to either CRF or GnRH in the acute secretion experiments.

In two additional series of experiments, the nonspecific effects of unconjugated gelonin toxin by itself and unconjugated gelonin toxin in the presence of [Nle$^{21,38}$,Arg$^{36}$]-rCRF are tested in a similar procedure. In one series, cells are pretreated with either B-PJ or unconjugated gelonin at final concentrations of 2, 10 or 50 nM; in the other series, cells are pretreated with either β-PJ, 2 nM gelonin plus 40 nM [Nle$^{21,38}$,Arg$^{36}$]-rCRF (unconjugated) or 10 nM gelonin plus 200 nM [Nle$^{21,38}$,Arg$^{36}$]-rCRF (unconjugated). After 12 hours, the cells are washed and plated as described above. After three days in culture, the ACTH and LH secretory responses, as well as cellular ACTH and LH contents, are determined as described above. ACTH and LH are measured by radioimmunoassay as previously described.

The molecular ratios of methionine, tyrosine and glycine to norleucine obtained in the analysis of the CRF-gelonin conjugate indicate a ratio of 20 moles CRF analog per mole gelonin. Analysis of the molecular ratios of all the amino acids in the reaction product conformed almost exactly to the ratios calculated for 20 moles [Nle$^{21,38}$,ARG$^{36}$]-rCRF per mole gelonin. Radioimmunoassay of the cytotoxin indicate 30% potency, compared to both [Nle$^{21,38}$,Arg$^{36}$]-rCRF and to rat CRF (as assessed by the amount of peptide required to displace 50% of radio-labelled CRF). In experiments designed to assess the biological activity of the cytotoxic conjugate by measuring acute ACTH secretion, the EC$_{50}$ of the conjugate when calculated on the basis of 20 moles of [Nle$^{21,38}$,Arg$^{36}$]-rCRF per mole of the cytotoxic conjugate appears to be about the same as the EC$_{50}$ for the CRF analog.

The effects of the cytotoxin, the CRF analog and unconjugated gelonin on ACTH and LH content and secretion are compared. ACTH content in cells pretreated only with β-PJ vehicle is 13.7±2.4 ng/well. While ACTH content is significantly decreased by CRF pretreatment only at a concentration of 50 nM (by 40%), all concentrations of the cytotoxic-conjugate pretreatment markedly decrease ACTH content, by 63, 74 and 77% at 2, 10 and 50 nM, respectively. In contrast, neither CRF nor the cytotoxic conjugate has any significant effect on LH content, when values are compared to the content of cells pretreated with β-PJ vehicle (44.1±7.8 ng/well). Unconjugated gelonin at equivalent concentrations has minimal effect on ACTH and LH content.

Exposure of cells to CRF at all concentrations does not eliminate the ability of the cells to respond to subsequent exposure to CRF by secreting ACTH. In contrast, pretreatment with the cytotoxic-conjugate at all doses eliminates the ACTH response to CRF. Pretreatment with CRF has no effect on the LH-secretory response to GnRH; only following pretreatment with the highest concentration of the cytotoxic conjugate is there any significant effect on GnRH-stimulated LH secretion (12.0±2.1 ng/4 h compared to 19.8±2.7 ng/4 h). Neither the ACTH- nor LH-secretory responses are statistically significantly altered by pretreatment with unconjugated gelonin. Pretreatment of cells with unconjugated gelonin plus the CRF analog in combination does not eliminate the ACTH secretory response to subsequent stimulation with CRF. Cells pretreated with 2 nM gelonin plus 40 nM of the CRF analog secrete ACTH at 3.3 times the basal rate in response to CRF 3 days following the pretreatment, whereas cells pretreated with 50 nM CRF alone secrete ACTH at 3.7 times the basal rate in response to CRF. Cells pretreated with 10 nM gelonin plus 200 nM of the CRF analog are able to secrete ACTH at more than double the basal rate in response to CRF. The ACTH secretory responses to CRF, both in cells pretreated with 2 nM gelonin plus 40 nM of the CRF analog and in cells pretreated with 10 nM elonin plus 200 nM of the CRF analog are significantly greater than the responses in cells pretreated with 2nM or 10 nM of the cytotoxic-conjugate.

EXAMPLE V

The conjugation of the CRF analog from Example I to ricin A chain using glutaraldehyde is carried out in a manner generally described in Example IV. Testing of the conjugate as set forth therein shows that it is biologically active to selectively eliminate CRF Target Cells.

EXAMPLE VI

The conjugation of the CRF analog of Example II to gelonin using glutaraldehyde is carried out in a manner generally described in Example IV. Testing of the conjugate as set forth therein shows that it is biologically active to selectively eliminate CRF Target Cells.

EXAMPLE VII

The peptide [Gly$^1$, Leu$^{33}$, Glu$^{40}$]-rCRF having the formula:
H-Gly-Glu-Glu-Pro-Pro-Ile-Ser-Leu-Asp-Leu-Thr-Phe-His-Leu Leu-Arg-Glu-Val-Leu-Glu-Met-Ala-Arg-Ala-Glu-Gln-Leu-Ala -Gln-Gln-Ala-His-Leu-Asn-Arg-Arg-Leu-Met-Glu-Glu-Ile-NH$_2$ is synthesized. Testing in accordance with the general procedure set forth in Example III shows that it likewise stimulates the secretion of ACTH and β-END-LI.

The conjugation of this CRF analog to ricin A chain using glutaraldehyde is carried out in a manner generally described in Example IV. Testing of the conjugate as set forth therein shows that it is biologically active to selectively eliminate CRF Target Cells.

EXAMPLE VIII

The peptide [des Ser$^1$-Glu$^2$-Glu$^3$, Leu$^{33}$, Arg$^{36}$, Glu$^{40}$]-rCRF having the formula:
H-Pro-Pro-Ile-Ser-Leu-Asp-Leu-Thr-Phe-His-Leu-Leu-Arg-Glu-Val -Leu-Glu-Met-Ala-Arg-Ala-Glu-Gln-Leu-Ala-Gln-Gln-Ala-His -Leu-Asn-Arg-Arg-Leu-Met-Glu-Glu-Ile-NH$_2$ is synthesized. Testing in accordance with the general procedure set forth in Example III shows that it likewise stimulates the secretion of ACTH and β-END-LI.

The conjugation of this CRF analog to ricin A chain using glutaraldehyde is carried out in a manner generally described in Example IV. Testing of the conjugate as set forth therein shows that it is biologically active to selectively eliminate CRF Target Cells.

EXAMPLE IX

The peptide [Nle$^{21,38}$, Glu$^{29}$, Arg$^{36}$]-rCRF having the formula:
H-Ser-Glu-Glu-Pro-Pro-Ile-Ser-Leu-Asp-Leu-Thr-Phe-His-Leu-Leu -Arg-Glu-Val-Leu-Glu-Nle-Ala-Arg-Ala-Glu-Gln-Leu-Ala -Glu-Gln-Ala-His-Ser-Asn-Arg-Arg-Leu-Nle-Glu-Ile-Ile-NH$_2$ is synthesized. Testing in accordance with the general procedure set forth in Example III shows that it likewise stimulates the secretion of ACTH and β-END-LI.

The conjugation of this CRF analog to gelonin using glutaraldehyde is carried out in a manner generally described in Example IV. Testing of the conjugate as set forth therein shows that it is biologically active to selectively eliminate CRF Target Cells.

EXAMPLE X

The peptide [Thr$^{22}$, Glu$^{29,40}$, Arg$^{36}$]-rCRF having the formula:
H-Ser-Glu-Glu-Pro-Pro-Ile-Ser-Leu-Asp-Leu-Thr-Phe-His-Leu-Leu -Arg-Glu-Val-Leu-Glu-Met-Thr-Arg-Ala-Glu-Gln-Leu-Ala-Glu -Gln-Ala-His-Ser-Asn-Arg-Arg-Leu-Met-Glu-Glu-Ile-NH$_2$ is synthesized. Testing in accordance with the general procedure set forth in Example III shows that it likewise stimulates the secretion of ACTH and β-END-LI.

The conjugation of this CRF analog to gelonin using glutaraldehyde is carried out in a manner generally described in Example IV. Testing of the conjugate as set forth therein shows that it is biologically active to selectively eliminate CRF Target Cells.

EXAMPLE XI

The peptide [Val$^1$, Ser$^2$, Arg$^{36}$, Glu$^{40}$]-rCRF having the formula:
H-Val-Ser-Glu-Pro-Pro-Ile-Ser-Leu-Asp-Leu-Thr-Phe-His-Leu-Leu -Arg-Glu-Val-Leu-Glu-Met-Ala-Arg-Ala-Glu-Gln-Leu-Ala-Gln -Gln-Ala-His-Ser-Asn-Arg-Arg-Leu-Met-Glu-Glu-Ile-NH$_2$ is synthesized. Testing in accordance with the general procedure set forth in Example III shows that it likewise stimulates the secretion of ACTH and β-END-LI.

The conjugation of this CRF analog to ricin A chain using glutaraldehyde is carried out in a manner generally described in Example IV. Testing of the conjugate as set forth therein shows that it is biologically active to selectively eliminate CRF Target Cells.

EXAMPLE XII

The peptide [Glu$^9$, Nle$^{21,38}$, Glu$^{29}$, Leu$^{33}$, Arg$^{36}$]-rCRF having the formula:
H-Ser-Glu-Glu-Pro-Pro-Ile-Ser-Leu-Glu-Leu-Thr-Phe-His-Leu-Leu -Arg-Glu-Val-Leu-Glu-Nle-Ala-Arg-Ala-Glu-Gln-Leu-Ala-Glu -Gln-Ala-His-Leu-Asn-Arg-Arg-Leu-Nle-Glu-Ile-Ile-NH$_2$ is synthesized. Testing in accordance with the general procedure set forth in Example III shows that it likewise stimulates the secretion of ACTH and β-END-LI.

The conjugation of this CRF analog to gelonin using glutaraldehyde is carried out in a manner generally described in Example IV. Testing of the conjugate as set forth therein shows that it is biologically active to selectively eliminate CRF Target Cells.

EXAMPLE XIII

The peptide [Nle$^8$, Ser$^{11}$, Leu$^{33}$, Arg$^{36}$, Glu$^{40}$]-rCRF having the formula:
H-Ser-Glu-Glu-Pro-Pro-Ile-Ser-Nle-Asp-Leu-Ser-Phe-His-Leu-Leu -Arg-Glu-Val-Leu-Glu-Met-Ala-Arg-Ala-Glu-Gln-Leu-Ala-Gln -Gln-Ala-His-Leu-Asn-Arg-Arg-Leu-Met-Glu-Glu-Ile-NH$_2$ is synthesized. Testing in accordance with the general procedure set forth in Example III shows that it likewise stimulates the secretion of ACTH and β-END-LI.

The conjugation of this CRF analog to ricin A chain using glutaraldehyde is carried out in a manner generally described in Example IV. Testing of the conjugate as set forth therein shows that it is biologically active to selectively eliminate CRF Target Cells.

EXAMPLE XIV

The peptide [Nle$^{21}$, Har$^{23}$, Leu$^{33}$, Glu$^{40}$, Nle$^{41}$]-rCRF having the formula:
H-Ser-Glu-Glu-Pro-Pro-Ile-Ser-Leu-Asp-Leu-Thr-Phe-His-Leu-Leu -Arg-Glu-Val-Leu-Glu-Nle-Ala-Har-Ala-Glu-Gln-Leu-Ala-Gln -Gln-Ala-His-Leu-Asn-Arg-Arg-Leu-Met-Glu-Glu-Nle-NH$_2$ is synthesized. Testing in accordance with the general procedure set forth in Example III shows that it likewise stimulates the secretion of ACTH and β-END-LI.

The conjugation of this CRF analog to gelonin using glutaraldehyde is carried out in a manner generally described in Example IV. Testing of the conjugate as set forth therein shows that it is biologically active to selectively eliminate CRF Target Cells.

EXAMPLE XV

The peptide [des Ser$^1$, des Gln$^3$, Nle$^{12}$, Glu$^{29}$, ]-rCRF having the formula:
H-Glu-Pro-Pro-Ile-Ser-Leu-Asp-Leu-Thr-Nle-His-Leu-Leu-Arg-Glu -Val-Leu-Glu-Met-Ala-Arg-Ala-Glu-Gln-Leu-Ala-Glu-Gln-Ala -His-Ser-Asn-Arg-Arg-Leu-Met-Glu-Ile-Ile-NH$_2$ is synthesized. Testing in accordance with the general procedure set forth in Example III shows that it likewise stimulates the secretion of ACTH and β-END-LI.

The conjugation of this CRF analog to gelonin using glutaraldehyde is carried out in a manner generally described in Example IV. Testing of the conjugate as set forth therein shows that it is biologically active to selectively eliminate CRF Target Cells.

EXAMPLE XVI

The peptide [des AA$^{1,2,3}$, Glu$^{29,40}$, Arg$^{36}$, Tyr$^{37}$]-rCRF(4-41) having the formula:
H-Pro-Pro-Ile-Ser-Leu-Asp-Leu-Thr-Phe-His-Leu-Leu-Arg-Glu -Val-Leu-Glu-Met-Ala-Arg-Ala-Glu-Gln-Leu-Ala-Glu-Gln-Ala -His-Ser-Asn-Arg-Arg-Tyr-Met-Glu-Glu-Ile-NH$_2$ is synthesized. Testing in accordance with the general procedure set forth in Example III shows that it likewise stimulates the secretion of ACTH and β-END-LI.

The conjugation of this CRF analog to gelonin using glutaraldehyde is carried out in a manner generally described in Example IV. Testing of the conjugate as set forth therein shows that it is biologically active to selectively eliminate CRF Target Cells.

EXAMPLE XVII

The peptide [Gln$^2$, Glu$^{29}$, Leu$^{38}$]-rCRF having the formula:
H-Ser-Gln-Glu-Pro-Pro-Ile-Ser-Leu-Asp-Leu-Thr-Phe-His-Leu-Leu -Arg-Glu-Val-Leu-Glu-Met-Ala-Arg-Ala-Glu-Gln-Leu-Ala-Glu -Gln-Ala-His-Ser-Asn-Arg-Arg-Leu-Leu-Glu-Ile-Ile-NH$_2$ is synthesized. Testing in accordance with the general procedure set forth in Example III shows that it likewise stimulates the secretion of ACTH and β-END-LI.

The conjugation of this CRF analog to ricin A chain using glutaraldehyde is carried out in a manner generally described in Example IV. Testing of the conjugate as set forth therein shows that it is biologically active to selectively eliminate CRF Target Cells.

EXAMPLE XVIII

The peptide [Nle$^{21,38}$, Tyr$^{32}$, Leu$^{33}$, Arg$^{36}$, Glu$^{40}$]-rCRF having the formula:
H-Ser-Glu-Glu-Pro-Pro-Ile-Ser-Leu-Asp-Leu-Thr-Phe-His-Leu-Leu -Arg-Glu-Val-Leu-Glu-Nle-Ala-Arg-Ala-Glu-Gln-Leu-Ala-Gln -Gln-Ala-Tyr-Leu-Asn-Arg-Arg-Leu-Nle-Glu-Glu-Ile-NH$_2$ is synthesized. Testing in accordance with the general procedure set forth in Example III shows that it likewise stimulates the secretion of ACTH and β-END-LI.

The conjugation of this CRF analog to gelonin using glutaraldehyde is carried out in a manner generally described in Example IV. Testing of the conjugate as set forth therein shows that it is biologically active to selectively eliminate CRF Target Cells.

EXAMPLE XIX

The peptide [Arg$^{16,21,22,25,27}$, Ala$^{20}$, Glu$^{28}$, Ile$^{39,40}$]-sauvagine having the formula:
Glu-Gly-Pro-Pro-Ile-Ser-Ile-Asp-Leu-Ser-Leu-Glu-Leu-Leu-Arg -Arg-Met-Ile-Glu-Ala-Arg-Arg-Gln-Glu-Arg-Glu-Arg-Glu-Gln -Ala-Ala-Asn-Asn-Arg-Leu-Leu-Leu-Asp-Ile-Ile-NH$_2$ is synthesized. Testing in accordance with the general procedure set forth in Example III shows that it likewise stimulates the secretion of ACTH and β-END-LI.

The conjugation of this CRF analog to ricin A chain using glutaraldehyde is carried out in a manner generally described in Example IV. Testing of the conjugate as set forth therein shows that it is biologically active to selectively eliminate CRF Target Cells.

EXAMPLE XX

The peptide [Glu$^9$, Nle$^{18,21}$]-AAHC having the formula:
H-Ser-Gln-Glu-Pro-Pro-Ile-Ser-Leu-Glu-Leu-Thr-Phe-His-Leu -Leu-Arg-Glu-Nle-Leu-Glu-Nle-Ala-Arg-Ala-Glu-Gln-Glu-Ala -Glu-Gln-Ala-Ala-Leu-Asn-Arg-Leu-Leu-Leu-Glu-Glu-Ala-NH$_2$ is synthesized. Testing in accordance with the general procedure set forth in Example III shows that it likewise stimulates the secretion of ACTH and β-END-LI.

The conjugation of this CRF analog to gelonin using glutaraldehyde is carried out in a manner generally described in Example IV. Testing of the conjugate as set forth therein shows that it is biologically active to selectively eliminate CRF Target Cells.

EXAMPLE XXI

The peptide [Nle$^{18,21}$]-AAHC having the formula:
H-Ser-Gln-Glu-Pro-Pro-Ile-Ser-Leu-Asp-Leu-Thr-Phe-His-Leu -Leu-Arg-Glu-Nle-Leu-Glu-Nle-Ala-Arg-Ala-Glu-Gln-Glu-Ala -Glu-Gln-Ala-Ala-Leu-Asn-Arg-Leu-Leu-Leu-Glu-Glu-Ala-NH$_2$ is synthesized. Testing in accordance with the general procedure set forth in Example III shows that it likewise stimulates the secretion of ACTH and β-END-LI.

The conjugation of this CRF analog to gelonin using glutaraldehyde is carried out in a manner generally described in Example IV. Testing of the conjugate as set forth therein shows that it is biologically active to selectively eliminate CRF Target Cells.

EXAMPLE XXII

The peptide [D-Pro$^4$, Nle$^{18,21}$]-AAHC having the formula:
H-Ser-Gln-Glu-D-Pro-Pro-Ile-Ser-Leu-Asp-Leu-Thr-Phe-His-Leu -Leu-Arg-Glu-Nle-Leu-Glu-Nle-Ala-Arg-Ala-Glu-Gln-Glu-Ala -Glu-Gln-Ala-Ala-Leu-Asn-Arg-Leu-Leu-Leu-Glu-Glu-Ala-NH$_2$ is synthesized. Testing in accordance with the general procedure set forth in Example III shows that it likewise stimulates the secretion of ACTH and β-END-LI.

The conjugation of this CRF analog to gelonin using glutaraldehyde is carried out in a manner generally described in Example IV. Testing of the conjugate as set forth therein shows that it is biologically active to selectively eliminate CRF Target Cells.

EXAMPLE XXIII

The peptide [D-Tyr$^3$, D-Pro$^4$, Nle$^{18,21}$]-AAHC having the formula:
H-Ser-Gln-D-Tyr-D-Pro-Pro-Ile-Ser-Leu-Asp-Leu-Thr-Phe-His-Leu -Leu-Arg-Glu-Nle-Leu-Glu-Nle-Ala-Arg-Ala-Glu-Gln-Glu-Ala -Glu-Gln-Ala-Ala-Leu-Asn-Arg-Leu-Leu-Leu-Glu-Glu-Ala-NH$_2$ is synthesized. Testing in accordance with the general procedure set forth in Example III shows that it likewise stimulates the secretion of ACTH and β-END-LI.

The conjugation of this CRF analog to ricin A chain using glutaraldehyde is carried out in a manner generally described in Example IV. Testing of the conjugate as set forth therein shows that it is biologically active to selectively eliminate CRF Target Cells.

EXAMPLE XXIV

The peptide [Glu$^{2,13,22}$, Leu$^{12}$, Har$^{23}$, Lys$^{26}$]-AAHC having the formula:
H-Ser-Glu-Glu-Pro-Pro-Ile-Ser-Leu-Asp-Leu-Thr-Leu-Glu-Leu -Leu-Arg-Glu-Met-Leu-Glu-Met-Glu-Har-Ala-Glu-Arg-Glu-Ala -Glu-Gln-Ala-Ala-Leu-Asn-Arg-Leu-Leu-Leu-Glu-Glu-Ala-NH$_2$. Testing in accordance with the general procedure set forth in Example III shows that it likewise stimulates the secretion of ACTH and β-END-LI.

The conjugation of this CRF analog to ricin A chain using glutaraldehyde is carried out in a manner generally described in Example IV. Testing of the conjugate as set forth therein shows that it is biologically active to selectively eliminate CRF Target Cells.

EXAMPLE XXV

The synthetic peptide [Ala13]-AAHC having the formula:
H-Ser-Gln-Glu-Pro-Pro-Ile-Ser-Leu-Asp-Leu-Thr-Phe-Ala-Leu -Leu-Arg-Glu-Met-Leu-Glu-Met-Ala-Arg-Ala-Glu-Gln-Glu-Ala -Glu-Gln-Ala-Ala-Leu-Asn-Arg-Leu-Leu-Leu-Glu-Glu-Ala-NH$_2$ is synthesized. Testing in accordance with the general procedure set forth in Example III shows that it likewise stimulates the secretion of ACTH and β-END-LI.

The conjugation of this CRF analog to ricin A chain using glutaraldehyde is carried out in a manner generally described in Example IV. Testing of the conjugate as set forth therein shows that it is biologically active to selectively eliminate CRF Target Cells.

EXAMPLE XXVI

The peptide [Leu$^{12}$, Glu$^{13}$, Tyr$^{37}$]-AAHC having the formula:
H-Ser-Gln-Glu-Pro-Pro-Ile-Ser-Leu-Asp-CML-Thr-Leu-Glu-Leu -Leu-Arg-Glu-Met-Leu-Glu-Met-Ala-Arg-Ala-Glu-Gln-Glu-Ala -Glu-Gln-Ala-Ala-Leu-Asn-Arg-Leu-Tyr-Leu-Glu-Glu-Ala-NH$_2$. Testing in accordance with the general procedure set forth in Example III shows that it likewise stimulates the secretion of ACTH and β-END-LI.

The conjugation of this CRF analog to gelonin using glutaraldehyde is carried out in a manner generally described in Example IV. Testing of the conjugate as set forth therein shows that it is biologically active to selectively eliminate CRF Target Cells.

EXAMPLE XXVII

The peptide [CML$^{10,14,19,27,33,38}$, Har$^{36}$]-AAHC having the formula:
H-Ser-Gln-Glu-Pro-Pro-Ile-Ser-Leu-Asp-CML-Thr-Phe-His-CML -Leu-Arg-Glu-Met-CML-Glu-Met-Ala-Arg-Ala-Glu-Gln-CML-Ala -Glu-Gln-Ala-Ala-CML-Asn-Arg-Har-Leu-CML-Glu-Glu-Ala-NH$_2$. Testing in accordance with the general procedure set forth in Example III shows that it likewise stimulates the secretion of ACTH and β-END-LI.

The conjugation of this CRF analog to gelonin using glutaraldehyde is carried out in a manner generally described in Example IV. Testing of the conjugate as set forth therein shows that it is biologically active to selectively eliminate CRF Target Cells.

EXAMPLE XXVIII

The peptide [CML$^{10,15,27,37}$,CMA$^{22,32,41}$]-AAHC having the formula:
H-Ser-Gln-Glu-Pro-Pro-Ile-Ser-Leu-Asp-CML-Thr-Phe-His-Leu -CML-Arg-Glu-Met-Leu-Glu-Met-CMA-Arg-Ala-Glu-Gln-CML-Ala -Glu-Gln-Ala-CMA-Leu-Asn-Arg-Leu-CML-Leu-Glu-Glu-CMA-NH$_2$. Testing in accordance with the general procedure set forth in Example III shows that it likewise stimulates the secretion of ACTH and β-END-LI.

The conjugation of this CRF analog to gelonin using glutaraldehyde is carried out in a manner generally described in Example IV. Testing of the conjugate as set forth therein shows that it is biologically active to selectively eliminate CRF Target Cells.

EXAMPLE XXIX

The peptide [D-Tyr$^3$, D-Pro$^4$, Nle$^{18,21}$]-AHC(3-41) having the formula:
H-D-Tyr-D-Pro-Pro-Ile-Ser-Leu-Asp-Leu-Thr-Phe-His-Leu-Leu-Arg -Glu-Nle-Leu-Glu-Nle-Ala-Arg-Ala-Glu-Gln-Glu-Ala -Glu-Gln-Ala-Ala-Leu-Asn-Arg-Leu-Leu-Leu-Glu-Glu-Ala-NH$_2$ is synthesized. Testing in accordance with the general procedure set forth in Example III shows that it stimulates the secretion of ACTH and β-END-LI.

The conjugation of this CRF analog to gelonin using glutaraldehyde is carried out in a manner generally described in Example IV. Testing of the conjugate as set forth therein shows that it is biologically active to selectively eliminate CRF Target Cells.

EXAMPLE XXX

The peptide [D-Pro$^4$, Nle$^{18,21}$]-AAHC(4-41) having the formula:
H-D-Pro-Pro-Ile-Ser-Leu-Asp-Leu-Thr-Phe-His-Leu-Leu-Arg-Glu -Nle-Leu-Glu-Nle-Ala-Arg-Ala-Glu-Gln-Glu-Ala-Glu-Gln-Ala -Ala-Leu-Asn-Arg-Leu-Leu-Leu-Glu-Glu-Ala-NH$_2$ is synthesized. Testing in accordance with the general procedure set forth in Example III shows that it stimulates the secretion of ACTH and β-END-LI.

The conjugation of this CRF analog to ricin A chain using glutaraldehyde is carried out in a manner generally described in Example IV. Testing of the conjugate as set forth therein shows that it is biologically active to selectively eliminate CRF Target Cells.

EXAMPLE XXXI

The peptide [Glu$^{22}$, Leu$^{12}$, Har$^{23,36}$]-AHC(4-41) having the formula:
H-Pro-Pro-Ile-Ser-Leu-Asp-Leu-Thr-Leu-His-Leu-Leu-Arg-Glu -Met-Leu-Glu-Met-Glu-Har-Ala-Glu-Gln-Glu-Ala-Glu-Gln-Ala -Ala-Leu-Asn-Arg-Har-Leu-Leu-Glu-Glu-Ala-NH$_2$ Testing in accordance with the general procedure set forth in Example III shows that it likewise stimulates the secretion of ACTH and β-END-LI.

The conjugation of this CRF analog to gelonin using glutaraldehyde is carried out in a manner generally described in Example IV. Testing of the conjugate as set forth therein shows that it is biologically active to selectively eliminate CRF Target Cells.

EXAMPLE XXXII

The peptide [Arg$^{23,36}$]-oCRF having the formula:
H-Ser-Gln-Glu-Pro-Pro-Ile-Ser-Leu-Asp-Leu-Thr-Phe-His-Leu-Leu -Arg-Glu-Val-Leu-Glu-Met-Thr-Arg-Ala-Asp-Gln-Leu-Ala-Gln -Gln-Ala-His-Ser-Asn-Arg-Arg-Leu-Leu-Asp-Ile-Ala-NH$_2$ is synthesized. Testing in accordance with the general procedure set forth in Example III shows that it stimulates the secretion of ACTH and β-END-LI.

The conjugation of this CRF analog to gelonin using glutaraldehyde is carried out in a manner generally described in Example IV. Testing of the conjugate as set forth therein shows that it is biologically active to selectively eliminate CRF Target Cells.

EXAMPLE XXXIII

The peptide [Nle$^{21}$, Arg$^{23,36}$]-oCRF having the formula:
H-Ser-Gln-Glu-Pro-Pro-Ile-Ser-Leu-Asp-Leu-Thr-Phe-His-Leu-Leu -Arg-Glu-Val-Leu-Glu-Nle-Thr-Arg-Ala-Asp-Gln-Leu-Ala-Gln -Gln-Ala-His-Ser-Asn-Arg-Arg-Leu-Leu-Asp-Ile-Ala-NH$_2$ is synthesized. Testing in accordance with the general procedure set forth in Example III shows that it likewise stimulates the secretion of ACTH and β-END-LI.

The conjugation of this CRF analog to gelonin using glutaraldehyde is carried out in a manner generally described in Example IV. Testing of the conjugate as set forth therein shows that it is biologically active to selectively eliminate CRF Target Cells.

EXAMPLE XXXIV

The peptide [Nle$^{18,21}$,Arg$^{23,28,36}$]-oCRF having the formula:
H-Ser-Gln-Glu-Pro-Pro-Ile-Ser-Leu-Asp-Leu-Thr-Phe-His-Leu-Leu -Arg-Glu-Nle-Leu-Glu-Nle-Thr-Arg-Ala-Asp-Gln-Leu-Arg-Gln -Gln-Ala-His-Ser-Asn-Arg-Arg-Leu-Leu-Asp-Ile-Ala-NH$_2$ is synthesized. Testing in accordance with the general procedure set forth in Example III shows that it likewise stimulates the secretion of ACTH and β-END-LI.

The conjugation of this CRF analog to ricin A chain using glutaraldehyde is carried out in a manner generally described in Example IV. Testing of the conjugate as set forth therein shows that it is biologically active to selectively eliminate CRF Target Cells.

EXAMPLE XXXV

The peptide [D-Tyr$^3$, Arg$^{23,36}$, CML$^{33}$]-oCRF(3-41) having the formula:
H-D-Tyr-Pro-Pro-Ile-Ser-Leu-Asp-Leu-Thr-Phe-His-Leu-Leu-Arg -Glu-Val-Leu-Glu-Met-Thr-Arg-Ala-Asp-Gln-Leu-Ala-Gln -Gln-Ala-His-CML-Asn-Arg-Arg-Leu-Leu-Asp-Ile-Ala-$NH_2$ is synthesized. Testing in accordance with the general procedure set forth in Example III shows that it likewise stimulates the secretion of ACTH and β-END-LI.

The conjugation of this CRF analog to ricin A chain using glutaraldehyde is carried out in a manner generally described in Example IV. Testing of the conjugate as set forth therein shows that it is biologically active to selectively eliminate CRF Target Cells.

EXAMPLE XXXVI

The peptide [Nle$^{18}$, Arg$^{23,36}$, Tyr$^{37}$, Glu$^{40}$]-oCRF(2-41) having the formula:
H-Gln-Glu-Pro-Pro-Ile-Ser-Leu-Asp-Leu-Thr-Phe-His-Leu-Leu -Arg-Glu-Nle-Leu-Glu-Met-Thr-Arg-Ala-Asp-Gln-Leu-Ala-Gln -Gln-Ala-His-Ser-Asn-Arg-Arg-Tyr-Leu-Asp-Glu-Ala-$NH_2$ is synthesized. Testing in accordance with the general procedure set forth in Example III shows that it likewise stimulates the secretion of ACTH and β-END-LI.

The conjugation of this CRF analog to ricin A chain using glutaraldehyde is carried out in a manner generally described in Example IV. Testing of the conjugate as set forth therein shows that it is biologically active to selectively eliminate CRF Target Cells.

EXAMPLE XXXVII

The peptide [D-Tyr$^3$, Nle$^{18,21}$]-AAHC(3-41) having the formula:
H-D-Tyr-Pro-Pro-Ile-Ser-Leu-Asp-Leu-Thr-Phe-His-Leu -Leu-Arg-Glu-Nle-Leu-Glu-Nle-Ala-Arg-Ala-Glu-Gln-Glu-Ala -Glu-Gln-Ala-Ala-Leu-Asn-Arg-Leu-Leu-Leu-Glu-Glu-Ala-$NH_2$ is synthesized. Testing in accordance with the general procedure set forth in Example III shows that it likewise stimulates the secretion of ACTH and β-END-LI.

The conjugation of this CRF analog to gelonin using glutaraldehyde is carried out in a manner generally described in Example IV. Testing of the conjugate as set forth therein shows that it is biologically active to selectively eliminate CRF Target Cells.

EXAMPLE XXXVIII

The peptide [Nle$^{18,21}$, ]-AAHC(5-41) having the formula:
H-Pro-Ile-Ser-Leu-Asp-Leu-Thr-Phe-His-Leu-Leu-Arg-Glu-Nle -Leu-Glu-Nle-Ala-Arg-Ala-Glu-Gln-Glu-Ala-Glu-Gln-Ala-Ala -Leu-Asn-Arg-Leu-Leu-Leu-Glu-Glu-Ala-$NH_2$ is synthesized. Testing in accordance with the general procedure set forth in Example III shows that it likewise stimulates the secretion of ACTH and β-END-LI.

The conjugation of this CRF analog to gelonin using glutaraldehyde is carried out in a manner generally described in Example IV. Testing of the conjugate as set forth therein shows that it is biologically active to selectively eliminate CRF Target Cells.

EXAMPLE XXXIX

The peptide [Nle$^{18,21}$, Arg$^{36}$]-AAHC(6-41) having the formula:
H-Ile-Ser-Leu-Asp-Leu-Thr-Phe-His-Leu-Leu-Arg-Glu-Nle-Leu -Glu-Nle-Ala-Arg-Ala-Glu-Gln-Glu-Ala-Glu-Gln-Ala-Ala-Leu -Asn-Arg-Arg-Leu-Leu-Glu-Glu-Ala-$NH_2$ is synthesized. Testing in accordance with the general procedure set forth in Example III shows that it likewise stimulates the secretion of ACTH and β-END-LI.

The conjugation of this CRF analog to gelonin using glutaraldehyde is carried out in a manner generally described in Example IV. Testing of the conjugate as set forth therein shows that it is biologically active to selectively eliminate CRF Target Cells.

EXAMPLE XL

The peptide [D-Pro$^4$, Nle$^{21,38}$, Arg$^{36}$]-rCRF(4-41) having the formula:
H-D-Pro-Pro-Ile-Ser-Leu-Asp-Leu-Thr-Phe-His-Leu-Leu-Arg-Glu -Val-Leu-Glu-Nle-Ala-Arg-Ala-Glu-Gln-Leu-Ala-Gln-Gln-Ala -His-Ser-Asn-Arg-Arg-Leu-Nle-Glu-Ile-Ile-$NH_2$ is synthesized. Testing in accordance with the general procedure set forth in Example III shows that it stimulates the secretion of ACTH and β-END-LI.

The conjugation of this CRF analog to gelonin using glutaraldehyde is carried out in a manner generally described in Example IV. Testing of the conjugate as set forth therein shows that it is biologically active to selectively eliminate CRF Target Cells.

EXAMPLE XLI

The synthesis of [Arg$^{36}$]-rCRF (9-41) having the formula: H-Asp-Leu-Thr-Phe-His-Leu-Leu-Arg-Glu-Val -Leu-Glu-Met-Ala-Arg-Ala-Glu-Gln-Leu-Ala-Gln-Gln-Ala -His-Ser-Asn-Arg-Arg-Leu-Met-Glu-Ile-Ile-$NH_2$ is conducted in a stepwise manner on a MBHA hydrochloride resin. Testing shows the peptide inhibits the secretion of ACTH.

The conjugation of this CRF analog to gelonin using glutaraldehyde is carried out in a manner generally described in Example IV. Testing of the conjugate as set forth therein shows that it is biologically active to selectively eliminate CRF Target Cells.

EXAMPLE XLII

The synthetic peptide AAHC(9-41) having the formula: H-Asp-Leu-Thr-Phe-His-Leu-Leu-Arg-Glu-Met-Leu-Glu -Met-Ala-Arg-Ala-Glu-Gln-Glu-Ala-Glu-Gln-Ala-Ala-Leu-Asn -Arg-Leu-Leu-Leu-Glu-Glu-Ala-$NH_2$ is synthesized generally in accordance with the procedure set forth in Example I. Testing shows the peptide inhibits the secretion of ACTH.

The conjugation of this CRF analog to gelonin using glutaraldehyde is carried out in a manner generally described in Example IV. Testing of the conjugate as set forth therein shows that it is biologically active to selectively eliminate CRF Target Cells.

EXAMPLE XLIII

The peptide [Arg$^{36}$]-rCRF(8-41) having the formula:
H-Leu-Asp-Leu-Thr-Phe-His-Leu-Leu-Arg-Glu-Val-Leu-Glu-Met -Ala-Arg-Ala-Glu-Gln-Leu-Ala-Gln-Gln-Ala-His-Ser-Asn-Arg -Arg-Leu-Met-Glu-Ile-Ile-$NH_2$ is synthesized. Testing shows that it inhibits the secretion of ACTH and β-END-LI.

The conjugation of this CRF analog to gelonin using glutaraldehyde is carried out in a manner generally described in Example IV. Testing of the conjugate as set forth therein shows that it is biologically active to selectively eliminate CRF Target Cells.

EXAMPLE XLIV

The peptide [Arg$^{36}$]-rCRF(10-41) having the formula:
H-Leu-Thr-Phe-His-Leu-Leu-Arg-Glu-Val-Leu-Glu-Met-Ala-Arg -Ala-Glu-Gln-Leu-Ala-Gln-Gln-Ala-His-Ser-Asn-Arg-Arg-Leu -Met-Glu-Ile-Ile-NH$_2$ is synthesized. Testing shows that it likewise inhibits the secretion of ACTH and β-END-LI.

The conjugation of this CRF analog to ricin A chain using glutaraldehyde is carried out in a manner generally described in Example IV. Testing of the conjugate as set forth therein shows that it is biologically active to selectively eliminate CRF Target Cells.

EXAMPLE XLV

The peptide [Ala$^{19}$, Thr$^{22}$, Arg$^{36}$]-hCRF (9-41) having the formula:
H-Asp-Leu-Thr-Phe-His-Leu-Leu-Arg-Glu-Val-Ala-Glu-Met-Thr-Arg -Ala-Glu-Gln-Leu-Ala-Gln-Gln-Ala-His-Ser-Asn-Arg-Arg-Leu -Met-Glu-Ile-Ile-NH$_2$ is synthesized. Testing shows that it likewise inhibits the secretion of ACTH and β-END-LI.

The conjugation of this CRF analog to ricin A chain using glutaraldehyde is carried out in a manner generally described in Example IV. Testing of the conjugate as set forth therein shows that it is biologically active to selectively eliminate CRF Target Cells.

EXAMPLE XLVI

The peptide [Arg$^{36}$]-Carp Urotensin I(8-41) having the formula:
H-Ile-Asp-Leu-Thr-Phe-His-Leu-Leu-Arg-Asn-Met-Ile-Glu-Met-Ala -Arg-Asn-Glu-Asn-Gln-Arg-Glu-Gln-Ala-Gly-Leu-Asn-Arg-Arg -Tyr-Leu-Asp-Glu-Val-NH$_2$ is synthesized. Testing shows that it inhibits the secretion of ACTH and β-END-LI.

The conjugation of this CRF analog to gelonin using glutaraldehyde is carried out in a manner generally described in Example IV. Testing of the conjugate as set forth therein shows that it is biologically active to selectively eliminate CRF Target Cells.

EXAMPLE XLVII

The peptide [Glu$^{13}$, Val$^{21}$, Arg$^{36}$]-rCRF (9-41) having the formula:
H-Asp-Leu-Thr-Phe-Glu-Leu-Leu-Arg-Glu-Val-Leu-Glu-Val-Ala-Arg -Ala-Glu-Gln-Leu-Ala-Gln-Gln-Ala-His-Ser-Asn-Arg-Arg-Leu -Met-Glu-Ile-Ile-NH$_2$ is synthesized. Testing shows that it likewise inhibits the secretion of ACTH and β-END-LI.

The conjugation of this CRF analog to gelonin using glutaraldehyde is carried out in a manner generally described in Example IV. Testing of the conjugate as set forth therein shows that it is biologically active to

EXAMPLE XLVIII

The peptide [Nle$^8$, Ser$^{11}$, Leu$^{33}$, Arg$^{36}$]-rCRF(8-41) having the formula:
H-Nle-Asp-Leu-Ser-Phe-His-Leu-Leu-Arg-Glu-Val-Leu-Glu-Met-Ala -Arg-Ala-Glu-Gln-Leu-Ala-Gln-Gln-Ala-His-Leu-Asn-Arg-Arg -Leu-Met-Glu-Ile-Ile-NH$_2$ is synthesized. Testing shows that it inhibits the secretion of ACTH and β-END-LI.

The conjugation of this CRF analog to ricin A chain using glutaraldehyde is carried out in a manner generally described in Example IV. Testing of the conjugate as set forth therein shows that it is biologically active to selectively eliminate CRF Target Cells.

EXAMPLE IL

The peptide [CML$^{10,15,27,37}$, CMA$^{22,32,41}$]-AAHC(9-41) having the formula: H-Asp-CML-Thr-Leu-Glu -CML-CML-Arg-Glu-Met-CML-Glu-Met-CMA-Arg-Ala-Glu-Gln-CML -Ala-Glu-Gln-Ala-CMA-CML-Asn-Arg-Leu-CML-Leu-Glu-Glu-CMA-NH$_2$ Testing shows that it inhibits the secretion of ACTH and β-END-LI.

The conjugation of this CRF analog to gelonin using glutaraldehyde is carried out in a manner generally described in Example IV. Testing of the conjugate as set forth therein shows that it is biologically active to selectively eliminate CRF Target Cells.

EXAMPLE L

The peptide [Nle$^{18,21}$]-AAHC(9-41) having the formula: H-Asp-Leu-Thr-Phe-His-Leu-Leu-Arg-Glu-Nle-Leu-Glu -Nle-Ala-Arg-Ala-Glu-Gln-Glu-Ala-Glu-Gln-Ala-Ala-Leu-Asn -Arg-Leu-Leu-Leu-Glu-Glu-Ala-NH$_2$ is synthesized. Testing shows that it likewise inhibits the secretion of ACTH and β-END-LI.

The conjugation of this CRF analog to ricin A chain using glutaraldehyde is carried out in a manner generally described in Example IV. Testing of the conjugate as set forth therein shows that it is biologically active to selectively eliminate CRF Target Cells.

EXAMPLE LI

The peptide [Glu$^{13}$,Nle$^{18,21}$]-AAHC(9-41) having the formula: H-Asp-Leu-Thr-Phe-Glu-Leu-Leu-Arg -Glu-Nle-Leu-Glu-Nle-Ala-Arg-Ala-Glu-Gln-Glu-Ala-Glu -Gln-Ala-Ala-Leu-Asn-Arg-Leu-Leu-Leu-Glu-Glu-Ala-NH$_2$ is synthesized. Testing shows that it likewise inhibits the secretion of ACTH and β-END-LI.

The conjugation of this CRF analog to ricin A chain using glutaraldehyde is carried out in a manner generally described in Example IV. Testing of the Conjugate as set forth therein shows that it is biologically active to selectively eliminate CRF Target Cells.

EXAMPLE LII

The peptide [Nle$^{18,21}$]-AAHC(8-41) having the formula: H-Leu-Asp-Leu-Thr-Phe-His-Leu-Leu-Arg-Glu-Nle-Leu -Glu-Nle-Ala-Arg-Ala-Glu-Gln-Glu-Ala-Glu-Gln-Ala-Ala-Leu -Asn-Arg-Leu-Leu-Leu-Glu-Glu-Ala-NH$_2$ is synthesized. Testing shows that it inhibits the secretion of ACTH and β-END-LI.

The conjugation of this CRF analog to gelonin using glutaraldehyde is carried out in a manner generally described in Example IV. Testing of the conjugate as set forth therein shows that it is biologically active to selectively eliminate CRF Target Cells.

EXAMPLE LIII

The peptide [Nle$^{18,21}$]-AAHC(10-41) having the formula: H-Leu-Thr-Phe-His-Leu-Leu-Arg-Glu-Nle-Leu-Glu -Nle-Ala-Arg-Ala-Glu-Gln-Glu-Ala-Glu-Gln-Ala-Ala-Leu-Asn -Arg-Leu-Leu-Leu-Glu-Glu-Ala-NH$_2$ is synthesized. Testing shows that it inhibits the secretion of ACTH and β-END-LI.

The conjugation of this CRF analog to gelonin using glutaraldehyde is carried out in a manner generally described in Example IV. Testing of the conjugate as set forth therein shows that it is biologically active to selectively eliminate CRF Target Cells.

The cytotoxic CRF analog-conjugates described in the Examples selectively eliminate CRF target cells at concentrations that have minimal effects on other cell types. A number of toxins beside gelonin and the A chain of ricin may be used for the toxic subunit of the cytotoxin, e.g., diptheria toxins. Such toxins are potent protein synthesis inhibitors in cell free systems that generally have no effect in intact cells, except at very high concentrations or when introduced into cells as part of a toxic hybrid. Gelonin is preferred because its toxic properties are similar to that of ricin A chain, and it contains 21 lysine residues per molecule, which renders it more likely to bind to glutaraldehyde that has previously been linked to an analog such as [$Nle^{21,38}$, $Arg^{36}$]-rCRF.

[$Nle^{21,38}$, $Arg^{36}$]-rCRF contains only one free amino group, the amino terminal, which is in an area not required for biological activity. Thus, the most likely product to be formed quickly in the reaction between [$Nle^{21,38}$, $Arg^{36}$]-rCRF and glutaraldehyde is [OHC-$(CH_2)_5$-$Ser^1$,$Nle^{21,38}$,$Arg^{36}$]-rCRF. Other expected products include polymers of glutaraldehyde and dimers of the glutaraldehyde-linked CRF analog. Polymers of glutaraldehyde would be expected to be washed away by ultrafiltration. Dimers of glutaraldehyde-linked CRF analog might be present to react with gelonin in the next step of the synthesis, but they would likely be present in much smaller amounts than the amino terminal-linked glutaraldehyde. Any unreacted CRF analog would be expected to be washed through or to become bound nonspecifically to the 30,000 MW-cutoff ultrafiltration filter following the reaction with gelonin; thereby removed from the product.

Amino acid analysis of the final reaction product indicates a ratio of 20 moles [$Nle^{21,38}$, $Arg^{36}$]-rCRF per gelonin molecule. There are approximately 21 lysine residues in each gelonin molecule plus one amino terminal. Accordingly, ([$Nle^{21,38}$, $arg^{36}$]-rCRF)$_{20}$-gelonin is a possible formula for the conjugate.

The finding that the reaction product has 30% the potency of [$Nle^{21,38}$, $Arg^{36}$ -rCRF in the radioimmunoassay for CRF is also in line with the amino acid analysis. If all the bound CRF analog were 100% reactive with the anti-CRF antibody, the maximum reactivity of ([$Nle^{21,38}$, $Arg^{36}$]-rCRF)$_{20}$-gelonin on a per weight basis would be expected to be no higher than 76%.

The biological activity of the cytotoxic CRF analog, as assessed in the acute ACTH-secretory response, indicates that it binds to CRF receptors. The cytotoxic conjugate appears to be both more potent and to elicit a greater maximum effect on ACTH secretion than CRF. It is believed that the cytotoxic conjugate can cause pituitary cells to release ACTH by CRF-receptor-mediated bioactivity and by other mechanism(s) presumably which result in, or are a consequence of cell death. Once bound to cellular receptors, CRF is believed to become internalized, and this would appear to be the route by which the toxin is selectively introduced across cell membranes. Once inside CRF Target Cells, the cytotoxic CRF analog presumably acts in the same manner as does free gelonin in cell-free systems, namely by inactivating 60S ribosomal subunits. The CRF-gelonin conjugate retains toxicity despite having [$Nle^{21,38}$, $Arg^{36}$]-rCRF covalently attached at several points of its toxic subunit. CRF Target Cells likely contain proteases that degrade CRF, and the action of these enzymes might promote the toxicity of the hybrid by exposing the gelonin component, once it is bound to the cells.

Usually cytotoxicity is measured by the inhibition of the incorporation of radio-labelled nycleotides or amino acids into DNA or protein, or by similar methods. However, since corticotropes constitute a very small fraction of anterior pituitary cells, small differences in overall incorporation of radioactivity into protein and DNA cannot be unquestionably measured. Instead, efficacy of the gelonin-CRF analog conjugate as a cytotoxin is assessed by its effects on ACTH content and CRF-stimulated ACTH secretion. By these criteria, the conjugate has a potent effect on CRF Target Cells. While CRF and the conjugate are both potent stimulators of ACTH initially, after 3 days in culture, cells appear to recover from exposure to CRF but not to exposure to equal doses of the conjugate. In addition, because each molecule of the cytotoxic conjugate contains 20 molecules of the CRF analog and 1 molecule of gelonin, comparison of the ACTH-secretory responses in cells pretreated with 2 or 10 nM of the conjugate to the responses in cells pretreated with equivalent concentrations of the CRF analog and gelonin in unconjugated form in carried out. While pretreatment of cells with 40 and 200 nM of [$Nle^{21,38}$, $Arg^{36}$]-rCRF somewhat attenuates the ACTH-secretory response to subsequent stimulation with CRF, the effect of CRF nevertheless remains significant, in contrast to the total elimination of the response by pretreatment with the conjugate at much lower concentrations, 2 and 10 nM.

The specificity of the cytotoxic analog of CRF is demonstrated by its lack of effect on gonadotropes, a population of pituitary cells of roughly the same fraction of pituitary cells as corticotropes.

The invention thus provides a relatively simple method for the synthesis of a cytotoxic analog of a peptide hormone, i.e., CRF.

The conjugate may be injected into the circulatory system of a subject to deliver a dose of cytotoxin directly to the targeted cytoplasm of the cell by endocytosis after binding to a CRF receptor. This method is useful for the control of ACTH secretion in cases where CRF Target Cells are inappropriately secreting ACTH or where hypersecretion of CRF is occurring. The method is also useful for treating subjects with neoplastic diseases, such as certain cases of metastatic small cell carcinoma, where the tumor cells apparently express CRF receptors.

The efficiency with which a cytotoxin such as gelonin or ricin A chain can inhibit protein synthesis and consequently interfere with DNA synthesis is widely known. Thus, a dose of conjugate in the range of about 0.01 mg. to 100 mg. of conjugate/Kg of body weight will be sufficient to realize the desired clinical effect.

Although the invention has been described with regard to its preferred embodiments, which constitute the best mode presently known to the inventors, it should be understood that various changes and modifications as would be obvious to one having the ordinary skill in this art may be made without departing from the scope of the invention which is set forth in the claims appended hereto. For example, substitutions and modifications at other positions in the CRF peptide chain can be made in accordance with present or future developments without detracting from the potency of the analogs. It appears important that the amino acid sequence from about positions 6 through 41 or equivalents thereof be present in the synthetic peptide agonists, whereas the remainder of the molecule does not appear as critical. For instance, instead of the simple amide at the C-terminal, a lower alkyl-substituted amide, e.g. 1 to 4 carbons, i.e. methylamide, ethylamide, etc., may be incorporated. Likewise from one to ten additional amino acid residues can be included at the N-terminus without significantly adversely affecting biological potency. Such peptides are considered as equivalents which fall within the scope of the invention. Moreover, other dialdehydes or equivalent compounds, such as diacids, can be used instead of glutaraldehyde. Instead of substituting Arg for Lys within the peptide, the side chain basic character of Lys can be retained by suitably blocking the amine group, as by alkylation.

Particular features of the invention are emphasized in the claims which follow.

What is claimed is:

1. A CRF cytotoxic conjugate having high binding affinity for an intact call having a CRF receptor on its surface, said CRF cytotoxic conjugate comprising:
   (i) at least one CRF peptide analog devoid of sidechain primary amino groups which is selected from the group consisting of [$Nle^{21,38}$, $Arg^{36}$]-rCRF and [$Nle^{21,38}$, $Arg^{36}$]-oCRF and which has a binding affinity of $K_a = 1 \times 10^7 M^{-1}$ or less for a native CRF receptor, said at least one CRF analog having an N-terminal alpha-amino group;
   (ii) at least one dialdehyde coupling agent for each CRF peptide analog in said conjugate; and
   (iii) a gelonin cytotoxic protein having at least one primary amino group;.
   wherein each CRF peptide analog of said conjugate is covalently linked through the N-terminal alpha-amino group thereof to a first aldehyde group of said dialdehyde coupling agent and wherein a second aldehyde group of said coupling agent is covalently linked to said primary amino group of said gelonin cytotoxic protein.

2. A CRF cytotoxic conjugate according to claim 1 wherein the ratio of the molar concentration of said CRF peptide analog to the molar concentration of gelonin is approximately 20:1.

3. A CRF cytotoxic conjugate having a high binding affinity for an intact cell having a CRF receptor on its surface, said CRF cytotoxic conjugate comprising:
   (i) at least one CRF peptide analog, wherein said peptide analog has the formula [$Nle^{21,38}$, $Arg^{36}$]-rCRF;
   (ii) a glutaraldehyde coupling agent linked to every CRF analog peptide in said conjugate; and
   (iii) a single gelonin molecule having at least one available primary amino group;
   wherein each CRF peptide analog is linked by a covalent bond between the N-terminal alpha-amino group thereof and one carbonyl group of said glutaraldehyde coupling agent and the other carbonyl group of said glutaraldehyde coupling agent is covalently linked to a primary amino group of said gelonin molecule.

4. A CRF cytotoxic conjugate according to claim 3 wherein said gelonin molecule has a plurality of available primary amino groups and a plurality of CRF peptide analogs are linked to said gelonin molecule.

5. A CRF cytotoxic conjugate according to claim 4 wherein the ratio of the molar concentration of CRF peptide analogs to the molar concentration of gelonin is about 20:1.

* * * * *

UNITED STATES PATENT AND TRADEMARK OFFICE
CERTIFICATE OF CORRECTION

PATENT NO. : 5,132,111

DATED : July 21, 1992

INVENTOR(S) : Vale, Jr., et al.

It is certified that error appears in the above-identified patent and that said Letters Patent is hereby corrected as shown below:

Column 4, line 17, "Nle21,38" should be --Nle$^{21,38}$--. Column 4, line 42, after "receptors," delete --20--. Column 5, line 33, "NHz" should be --NH$_2$--. Column 7, line 49, "(X$^2$1)" should be --(X$^2$)--. Column 9, line 35, "OC" should be --0°C--. Column 11, line 23, after "therefore", delete --, which--. Column 11, line 29, "(4.C.)" should be --(4°C.)--. Column 11, line 42, after "cytotoxin", insert a period (.). Column 12, line 17, "Arg$^{35}$" should be --Arg$^{36}$--. Column 12, line 47, before "mmol.", insert --0.35--. Column 13, line 36, after "Leu(7.06)", insert --Phe(0.99), His(2.06) and Arg(4.27), which confirms that--. Column 14, line 41, "rate" should be --rats--. Column 14, line 51, in both instances, "βPJ" should be --β-PJ--. Column 14, line 62, "plates" should be --plated--. Column 15, line 14, "-lCRF" should be -- -rCRF --. Column 16, line 10, "elonin" should be --gelonin--. Column 16, line 30, after "Leu$^{33}$,", insert --Arg$^{36}$,--. Column 18, line 6, after "Leu$^{33}$,", insert --Arg$^{36}$,--. Column 18, line 22, after "Glu$^{29}$,", insert --Arg$^{36}$--. Column 18, line 55, after "Glu$^{29}$,", insert --Arg$^{36}$--. Column 19, line 21, at the beginning of the line, change "Glu" to --pGlu--. Column 20, line 47, "Ala13" should be --Ala$^{13}$--. Column 20, line 65, "CML" should be --Leu--. Column 25, line 57, after "to", insert --selectively eliminate CRF Target Cells.--. Column 28, line 4, correct the spelling of "nucleotides". Column 28, line 24, "in" should be --is--.

UNITED STATES PATENT AND TRADEMARK OFFICE
CERTIFICATE OF CORRECTION

PATENT NO. : 5,132,111

DATED : July 21, 1992

INVENTOR(S) : Vale, Jr., et al.

It is certified that error appears in the above-identified patent and that said Letters Patent is hereby corrected as shown below:

Column 29, line 19, "call" should be --cell--.

Signed and Sealed this

Twenty-eighth Day of September, 1993

*Attest:*

BRUCE LEHMAN

*Attesting Officer*      *Commissioner of Patents and Trademarks*